(12) United States Patent
Corghi

(10) Patent No.: US 8,113,049 B2
(45) Date of Patent: Feb. 14, 2012

(54) METHOD AND A MACHINE FOR BALANCING VEHICLE WHEELS

(75) Inventor: Remo Corghi, Correggio (IT)

(73) Assignee: Corghi S.p.A, Correggio (Reggio Emilia) (IT)

( * ) Notice: Subject to any disclaimer, the term of this patent is extended or adjusted under 35 U.S.C. 154(b) by 339 days.

(21) Appl. No.: 12/439,434

(22) PCT Filed: May 8, 2007

(86) PCT No.: PCT/IT2007/000340
§ 371 (c)(1),
(2), (4) Date: Sep. 1, 2009

(87) PCT Pub. No.: WO2008/032343
PCT Pub. Date: Mar. 20, 2008

(65) Prior Publication Data
US 2010/0005883 A1    Jan. 14, 2010

(30) Foreign Application Priority Data
Sep. 11, 2006 (IT) .............................. RE2006A0101

(51) Int. Cl.
*G01M 1/16* (2006.01)
(52) U.S. Cl. .......................................... 73/462; 353/13
(58) Field of Classification Search .................... 73/462, 73/146, 458, 468, 469, 470; 353/13, 69, 353/70
See application file for complete search history.

(56) References Cited

U.S. PATENT DOCUMENTS

| 4,480,471 | A | * | 11/1984 | Kogler et al. ................... 73/462 |
| 5,054,918 | A | * | 10/1991 | Downing et al. ......... 356/139.09 |
| 5,189,912 | A | * | 3/1993 | Quinlan et al. ................. 73/462 |
| 5,827,964 | A | * | 10/1998 | Douine et al. .................. 73/466 |
| 5,915,274 | A | * | 6/1999 | Douglas ......................... 73/462 |
| 6,122,957 | A | * | 9/2000 | Bux et al. ........................ 73/66 |
| 6,244,108 | B1 | * | 6/2001 | McInnes et al. ................ 73/462 |
| 6,484,574 | B1 | * | 11/2002 | Douglas et al. ................ 73/462 |
| 6,535,281 | B2 | * | 3/2003 | Conheady et al. ....... 356/139.09 |

(Continued)

FOREIGN PATENT DOCUMENTS
EP      0735356 A2    10/1996
(Continued)

*Primary Examiner* — Hezron E Williams
*Assistant Examiner* — Samir M Shah
(74) *Attorney, Agent, or Firm* — Browdy and Neimark, PLLC

(57) ABSTRACT

A method and a machine for balancing vehicle wheels with weights (18), the method comprising stages of: using a video camera (5, 6, 206) to frame a portion of a surface of a hub (101) of a wheel on which a weight (18) is to be applied, locating, in images of the hub (101) taken by the camera (5, 6, 206), at least a balancing plane (E1, E2) which is perpendicular to a rotation axis (A) of the wheel, piloting at least a pick-up device (8, 9, 209) such as to direct the at least a pick-up device (8, 9, 209) onto a point (P1, P2) of the hub (101) belonging to the balancing plane (E1, E2), detecting, by means of the pick-up device (8, 9, 209) characteristic geometric parameters of the hub (101) at the balancing plane (E1, E2), measuring an imbalance of the wheel, calculating, by means of an electronic calculator (4, 204) an entity of at least a weight (18) to be applied to the hub (101) at the balancing plane (E1, E2), and also calculating an angular position (T1, T2) of the weight (18) in the balancing plane (E1, E2).

29 Claims, 28 Drawing Sheets

U.S. PATENT DOCUMENTS

| | | | |
|---|---|---|---|
| 7,089,099 B2* | 8/2006 | Shostak et al. | 701/32 |
| 7,191,651 B2* | 3/2007 | Douglas et al. | 73/462 |
| 7,617,726 B2* | 11/2009 | Douglas | 73/462 |
| 7,684,027 B2* | 3/2010 | Douglas et al. | 356/155 |
| 7,686,403 B2* | 3/2010 | Douglas | 301/5.21 |
| 7,882,738 B2* | 2/2011 | Carpenter et al. | 73/460 |
| 7,976,107 B2* | 7/2011 | Okada et al. | 301/5.21 |
| 2004/0050159 A1* | 3/2004 | Corghi | 73/462 |
| 2004/0051864 A1* | 3/2004 | Braghiroli | 356/139.09 |
| 2004/0083810 A1* | 5/2004 | Racine | 73/462 |
| 2005/0052657 A1* | 3/2005 | Braghiroli | 356/602 |
| 2005/0052658 A1* | 3/2005 | Braghiroli | 356/602 |
| 2005/0055153 A1* | 3/2005 | Braghiroli | 701/124 |
| 2006/0017885 A1* | 1/2006 | Tang | 353/13 |
| 2006/0042380 A1 | 3/2006 | Douglas | |
| 2008/0119978 A1* | 5/2008 | Stieff et al. | 701/29 |
| 2009/0266160 A1* | 10/2009 | Jeffrey et al. | 73/455 |

FOREIGN PATENT DOCUMENTS

EP    1398611 A2    3/2004

\* cited by examiner

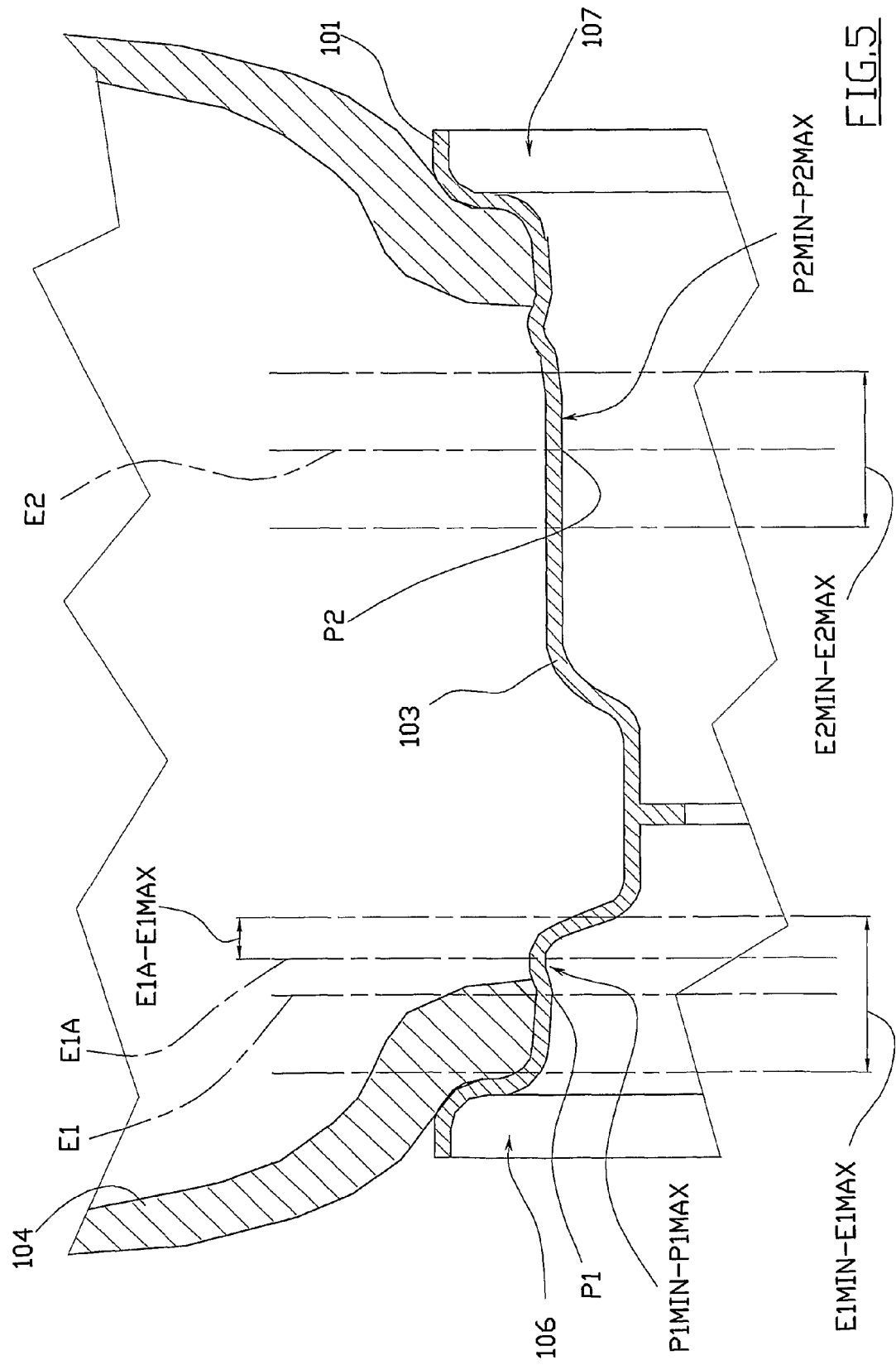

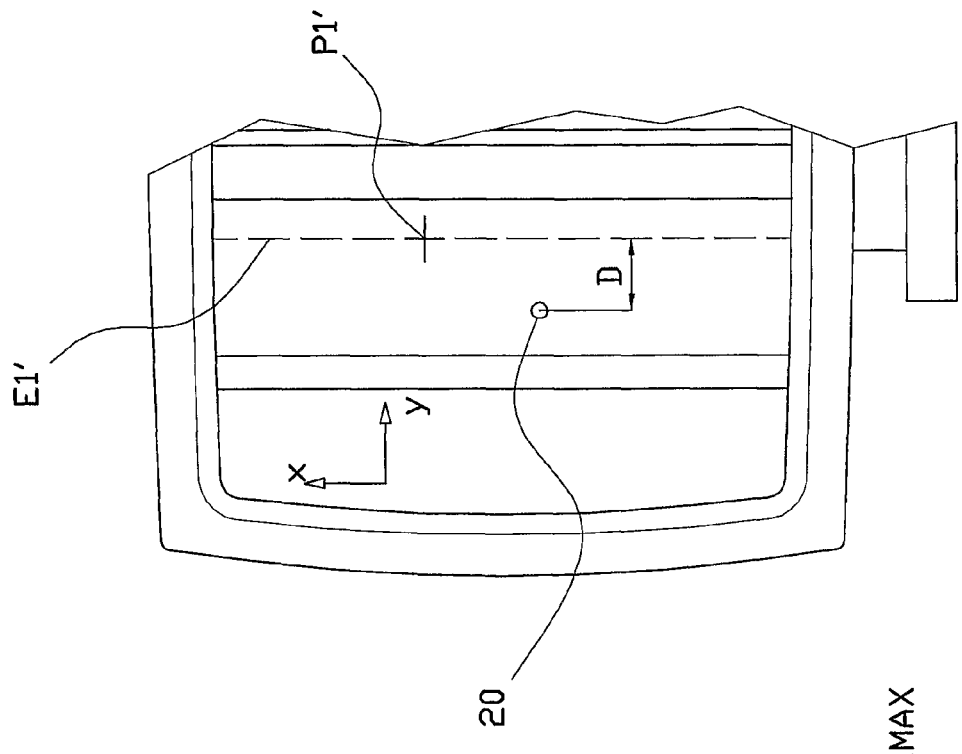
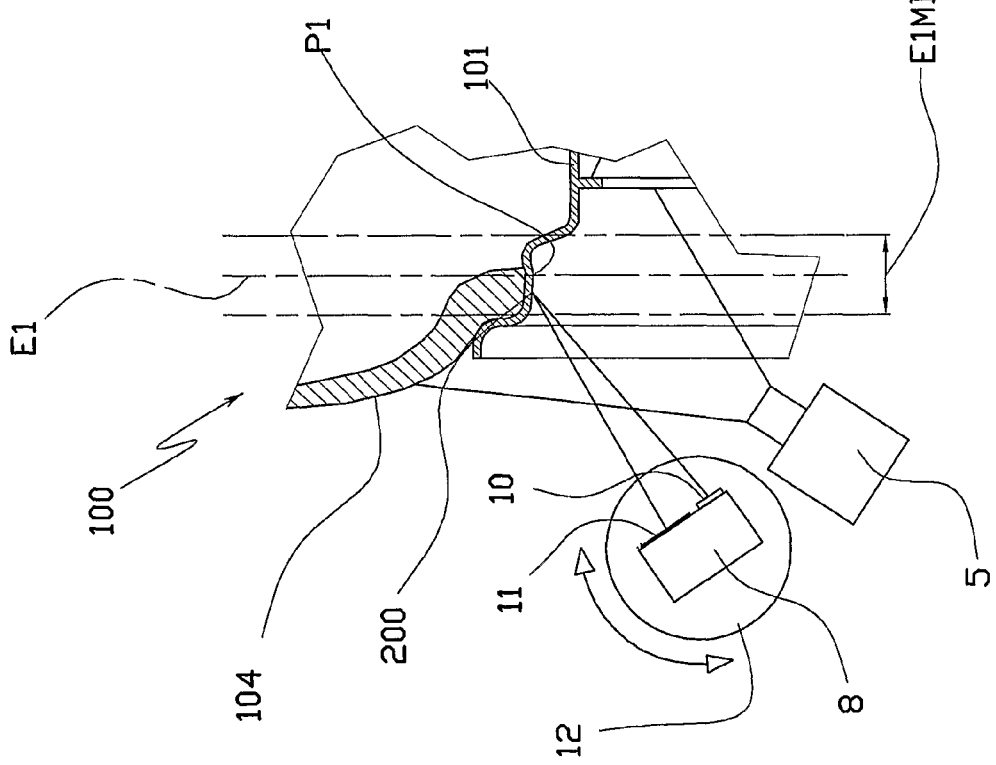
FIG.7
FIG.6

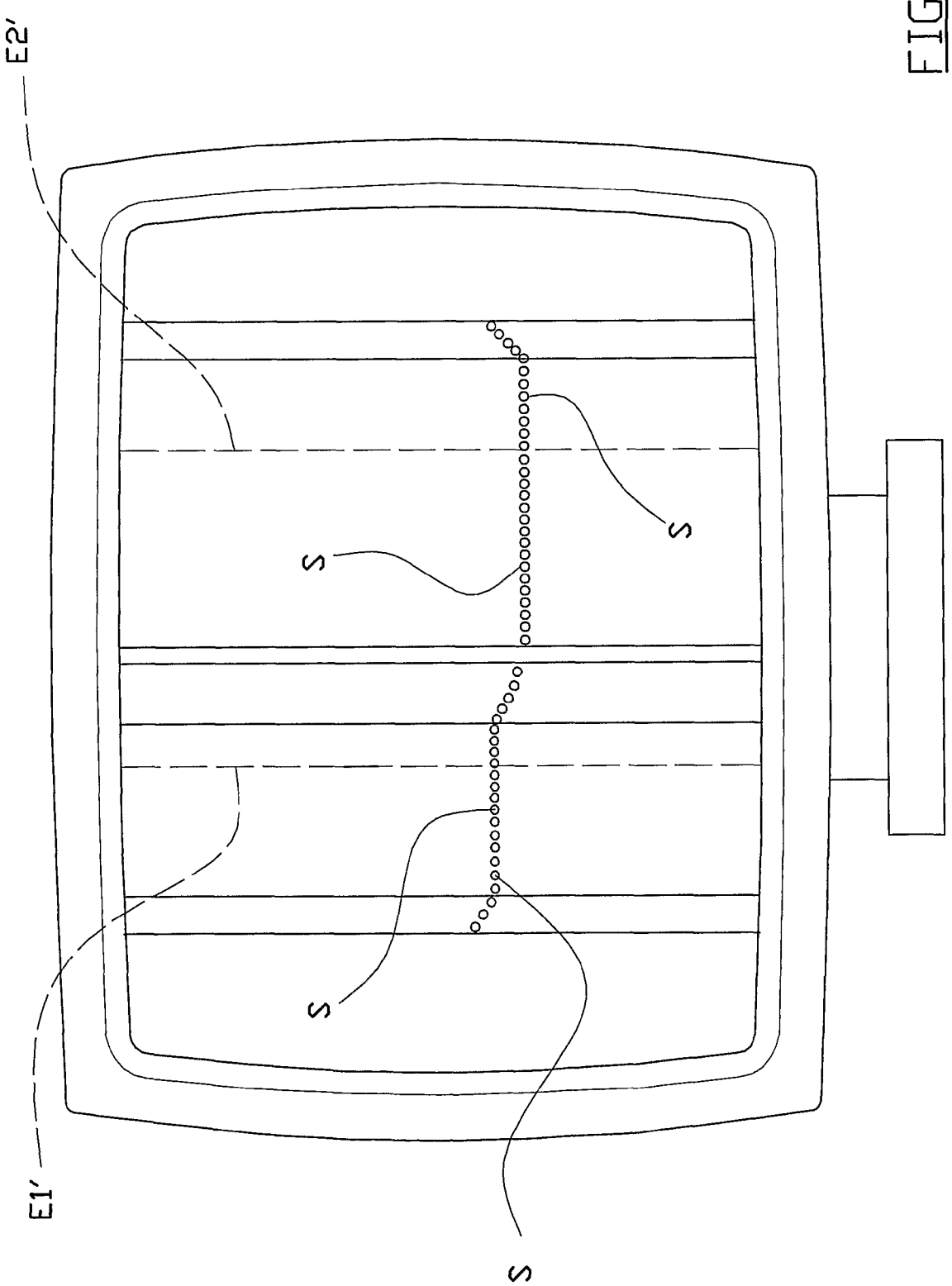

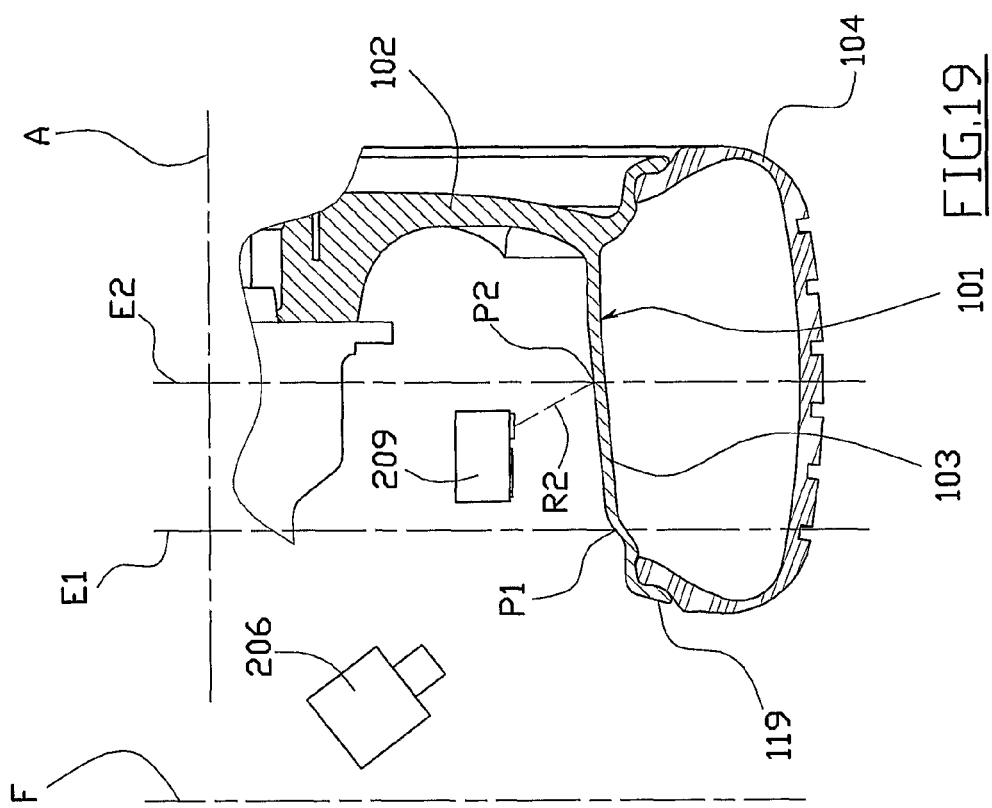
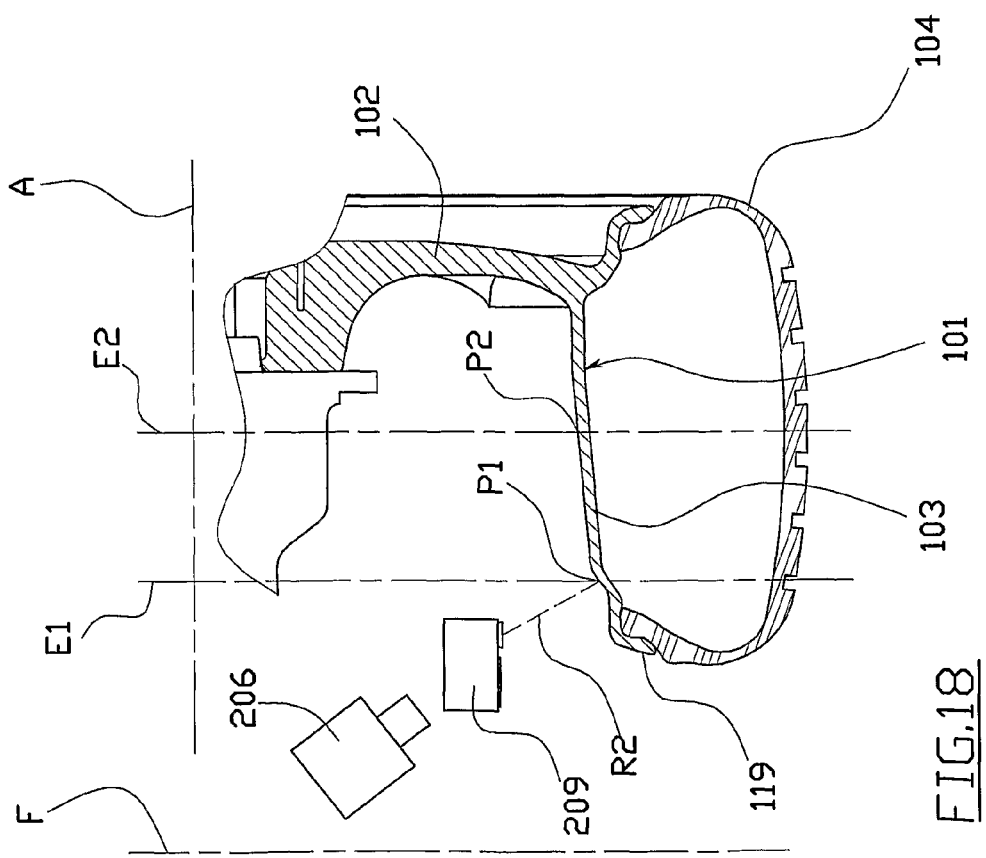

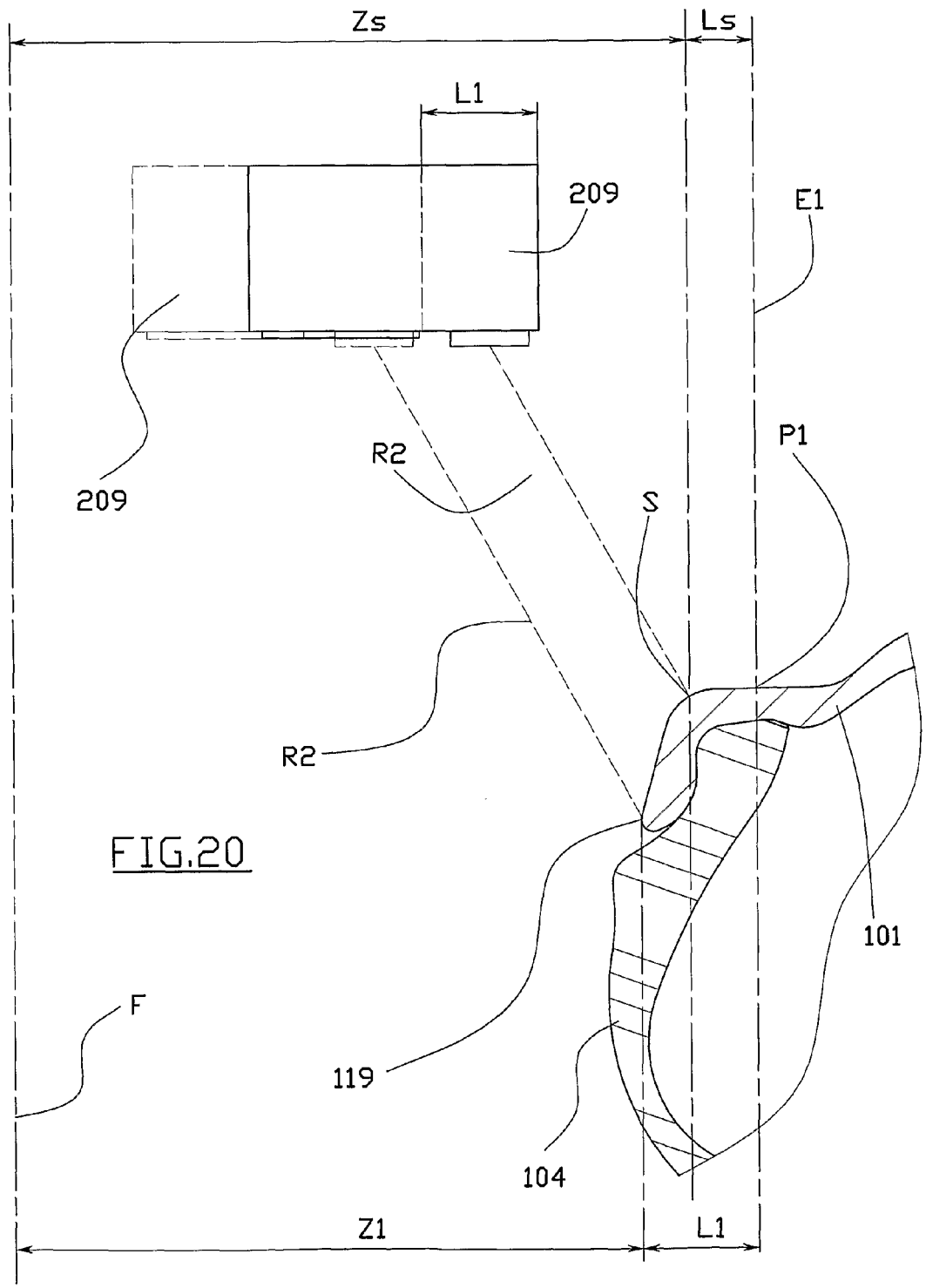

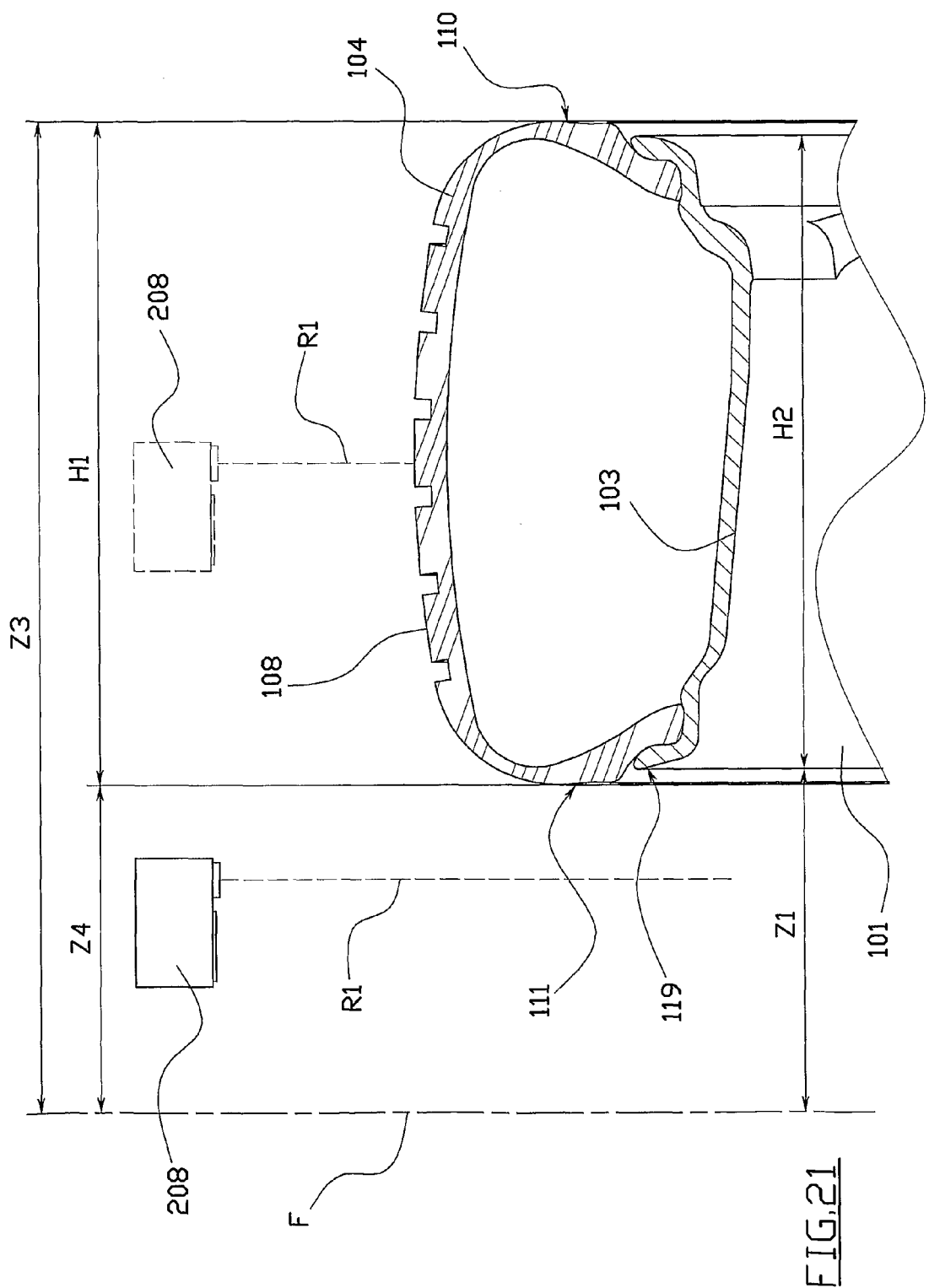

METHOD AND A MACHINE FOR BALANCING VEHICLE WHEELS

TECHNICAL FIELD

The invention relates to a method and a machine for balancing wheel vehicles by application of compensating weights.

BACKGROUND ART

As is known, the balancing of vehicle wheels includes identifying at least a plane which is perpendicular to the wheel axis, called the balancing plane, at which the weights will be applied on the wheel rim.

In particular, in order to perform static wheel balancing it is sufficient to identify one balancing plane alone, while in order to perform a dynamic balancing two distinct balancing planes must be identified, reciprocally distanced along the wheel axis.

An electronic calculator, connected to a measuring group belonging to the balancing machine, detects the wheel imbalance and calculates the entity of the weights according to the position of the balancing planes, as well as the angular position of the weights in the balancing planes themselves.

The identification of the balancing planes is generally done by measuring some geometrical parameters which are characteristic of the wheel hub to be balanced, after the wheel has been mounted on the balancing machine.

The geometric parameters are typically the hub diameter at each balancing plane and the distance of each balancing plane from a fixed reference plane of the balancing machine.

Usually these measurements are performed by feelers on the balancing machine, which are positioned manually by the operative according to the points on the hub which are comprised in the balancing plane in which he wishes to locate the weights.

The displacement of the feeler organs from a predetermined initial position is measured by special electronic systems which transmit the performed measurement to the electronic calculator which then processes the data.

Recent research in the field of wheel balancers has been especially directed at obtaining maximum automation of the balancing processes, so as to optimise the results and reduce error as well as manual intervention on the part of the operatives.

In this context, balancing machines have been devised which can make a totally automatic reading of the optimal balancing planes at which the weights should be applied on the rims.

These balancing machines are generally provided with special pick-up devices which are connected to the electronic calculator and can perform a scan of the hub profile, and acquire for each point thereon the geometric parameters required for the balancing operation.

The pick-up devices are generally aimed at detecting the spatial position of the points on the rim without direct contact with the points themselves, such as for example optical devices for measuring distances.

In this way, on the basis of the rim profile and other imbalances of the wheel measured by the measuring group, the electronic calculator is able automatically to identify the optimal balancing planes, without any need for feelers and without any direct intervention on the part of the operative.

Clearly these balancing machines are very expensive and complicated, and they do not always respond to market demand, where the need to have greater automation is generally accompanied by a need to have accessible prices.

Further, the scanning of the rim profile requires a relatively long time, which has an overall effect of slowing down the wheel balancing process.

The aim of the present invention is to solve the above-mentioned drawbacks in the prior art, by making available a method and a machine for vehicle wheel balancing, in which the determining of the balancing planes can be done semi-automatically, reducing the operative's manual contribution and improving the precision of the balancing, though remaining within the ambit of a simple, rational and inexpensive solution.

DISCLOSURE OF INVENTION

The aim 1s attained by the invention as it is characterised in the appended claims.

In general, the invention makes available a method for vehicle wheel balancing using compensating weights which comprises stages of:

using a video camera to frame a portion of the wheel hub on which the weights are to be applied, locating, in the images of the hub acquired by the camera, at least a balancing plane which is perpendicular to the wheel rotation axis, piloting at least a pick-up device in order to direct it onto a point on the hub belonging to the balancing plane identified in the images, using the pick-up device to detect the geometric parameters which are characteristic of the hub in the balancing plane, measuring the wheel imbalance, using an electronic calculator to calculate the entity of at least a weight to apply on the hub in the balancing plane, and the angular position of the weight in the balancing plane.

Obviously, in order to perform the dynamic balancing of the wheels, the method includes locating, in the images of the hub acquired by the camera, two distinct balancing planes which are perpendicular to the wheel axis, piloting the at least a pick-up device in order to direct it onto two points of the hub, each of which points belongs to a respective balancing plane located in the images, using the at least a pick-up device to detect the geometric parameters which are characteristic of the hub at the balancing planes and, after having measured the wheel imbalance, using the electronic calculator to detect the entity of at least two weights to be applied to the hub at the balancing planes, as well as the angular position of each weight at the respective balancing plane.

In a first embodiment of the invention, the state of located each balancing plane includes:

projecting onto a screen the image of the hub taken by the at least a camera, and arbitrarily selecting the balancing plane to be projected onto the screen.

Thanks to this solution, the operative's work is facilitated; he can simply select the balancing planes on the screen, and decide on the suitability of the various zones of the rim for receiving a weight.

Further, thanks to the pick-up device, the acquisition of the geometric characteristics of the hub at the selected balancing planes is done very precisely and rapidly, and without any direct contact with the hub.

A second embodiment of the invention comprises locating each balancing plane by identifying, in the images of the hub taken by the camera, a reference line which corresponds to a predetermined circumference of the hub surface, establishing the relative position which the balancing plane must have with respect to the predetermined circumference.

Thanks to this solution, the method can be performed autonomously by an electronic calculator connected to the camera, which calculator processes the images and proposes the planes for automatic balancing. In order to perform the above-described balancing method effectively, the invention makes available a balancing machine comprising a rotating shaft on a fixed structure, means for blocking the wheel on the rotating shaft, means for measuring the wheel imbalance, and an electronic calculator for calculating the entities of the weights to be applied on the rim at the at least a predetermined balancing plane which is perpendicular to the wheel axis, and the angular position of the weights in the balancing plane itself.

In particular, the balancing machine comprises at least a video camera for framing the portion of hub surface in which the weights are to be applied, a screen on which the images taken by the camera are projected, and at least a pick-up device, connected to the electronic calculator, which can be piloted in such a way that it comes directly onto a point of the hub which belongs to the balancing plane, for detecting the geometric parameters of the hub at the balancing plane itself.

In this context, the electronic calculator is preferably able to re-process the images taken by the cameras and in some embodiments it is also able automatically to control some regulating parameters of the cameras, among which for example the exposure and/or the focussing function.

BRIEF DESCRIPTION OF THE DRAWINGS

Further characteristics and advantages of the invention will better emerge from a reading of the following description, provided purely by way of non-limiting example, with the aid of the accompanying figures of the drawings, in which:

FIG. 5 is an enlarged detail of FIG. 3;

FIGS. 6 and 7 show two details respectively of FIGS. 5 and 4, during a same balancing process stage;

FIG. 8 is the screen of the machine of FIG. 1, while it is showing the basic image of the hub on which the points which can be selected are shown, in a particular embodiment of the invention;

FIGS. 18 and 19 illustrate the lateral pick-up device 209 in two successive moments of FIG. 17;

FIG. 20 is an enlarged detail of FIG. 17, illustrating how the lateral pick-up device 209 is displaced;

FIGS. 21, 22, 23, 24, 25 illustrate the functioning of the posterior pick-up device 298 during the identifying of the flanks of the tyre 104, in five possible alternatives;

Figure 12:
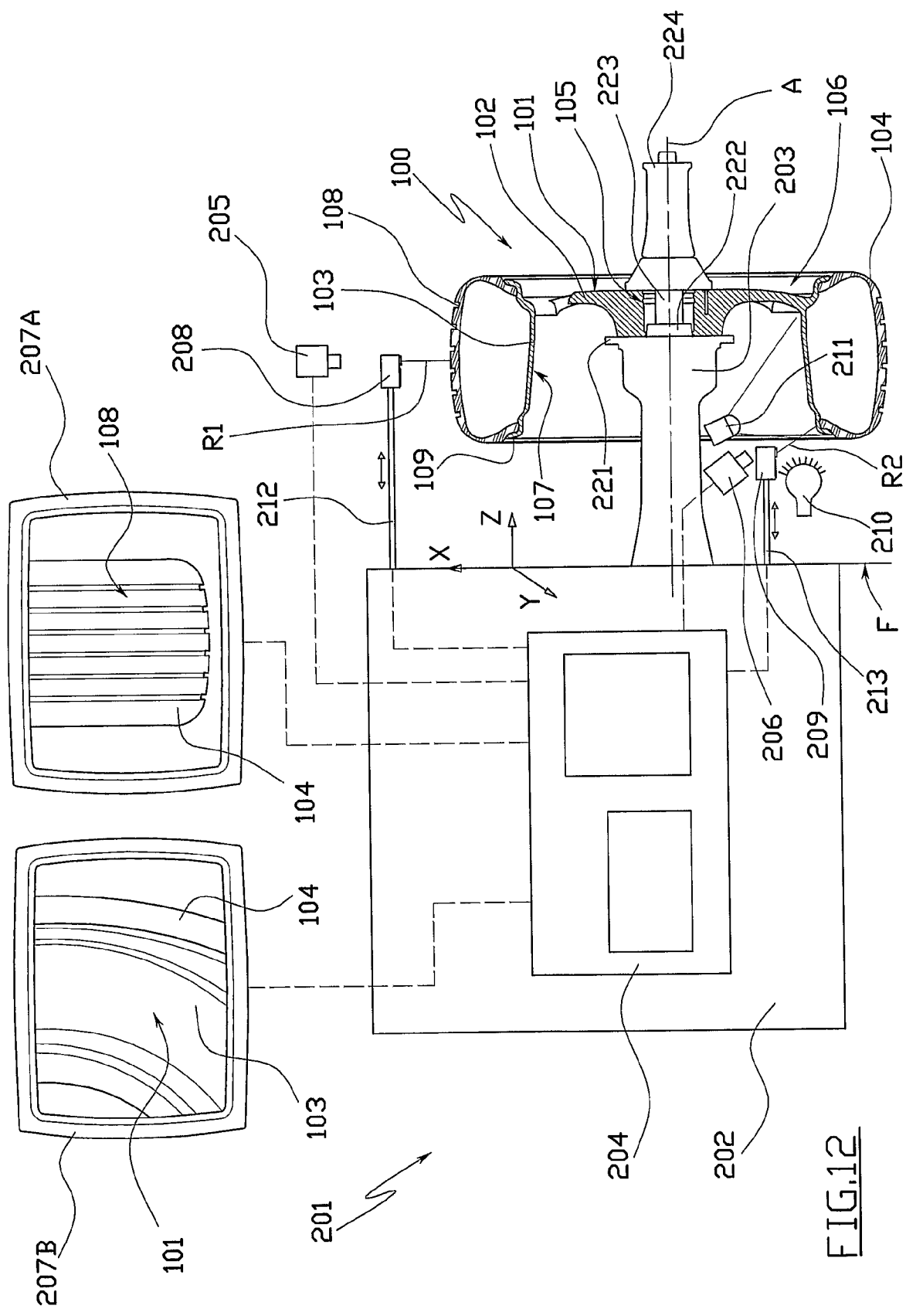
FIG. 12 illustrates a balancing machine in an alternative embodiment of the invention.
Figure 13:
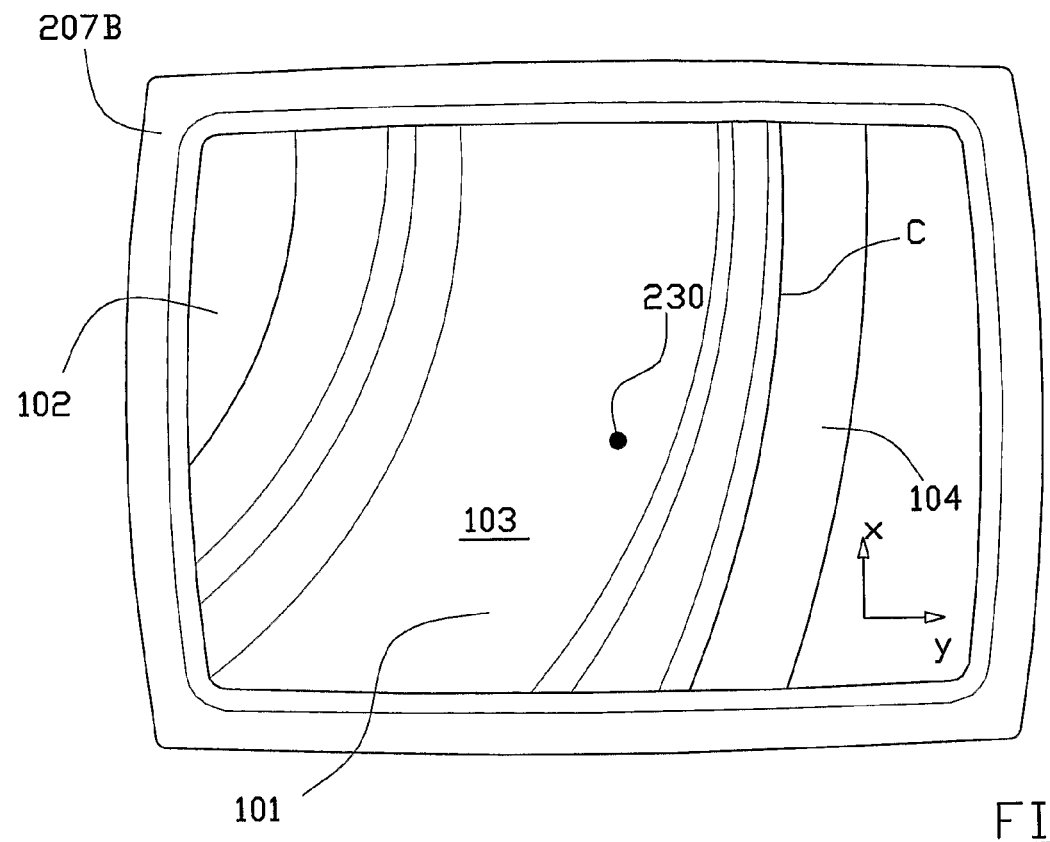
FIGS. 13, 14, 15 and 16 illustrate images taken by the lateral camera 206 during different operational stages of the machine of FIG. 12.
Figure 38:
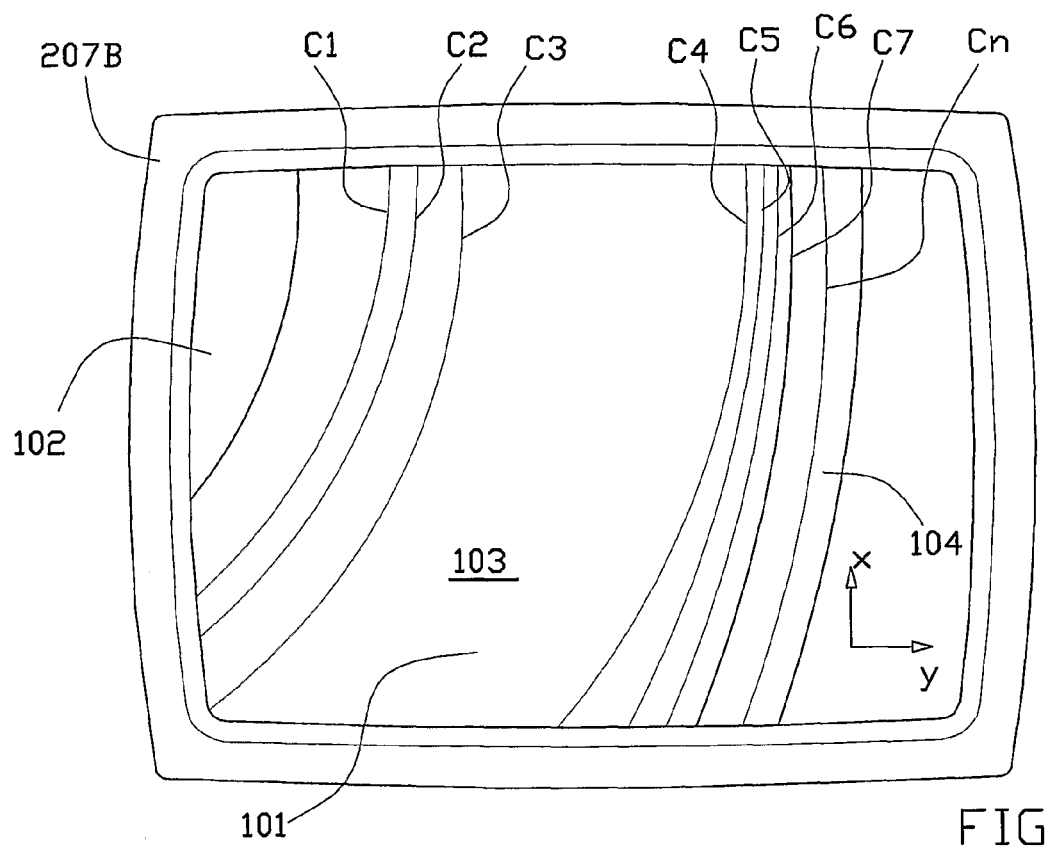
Figure 42:
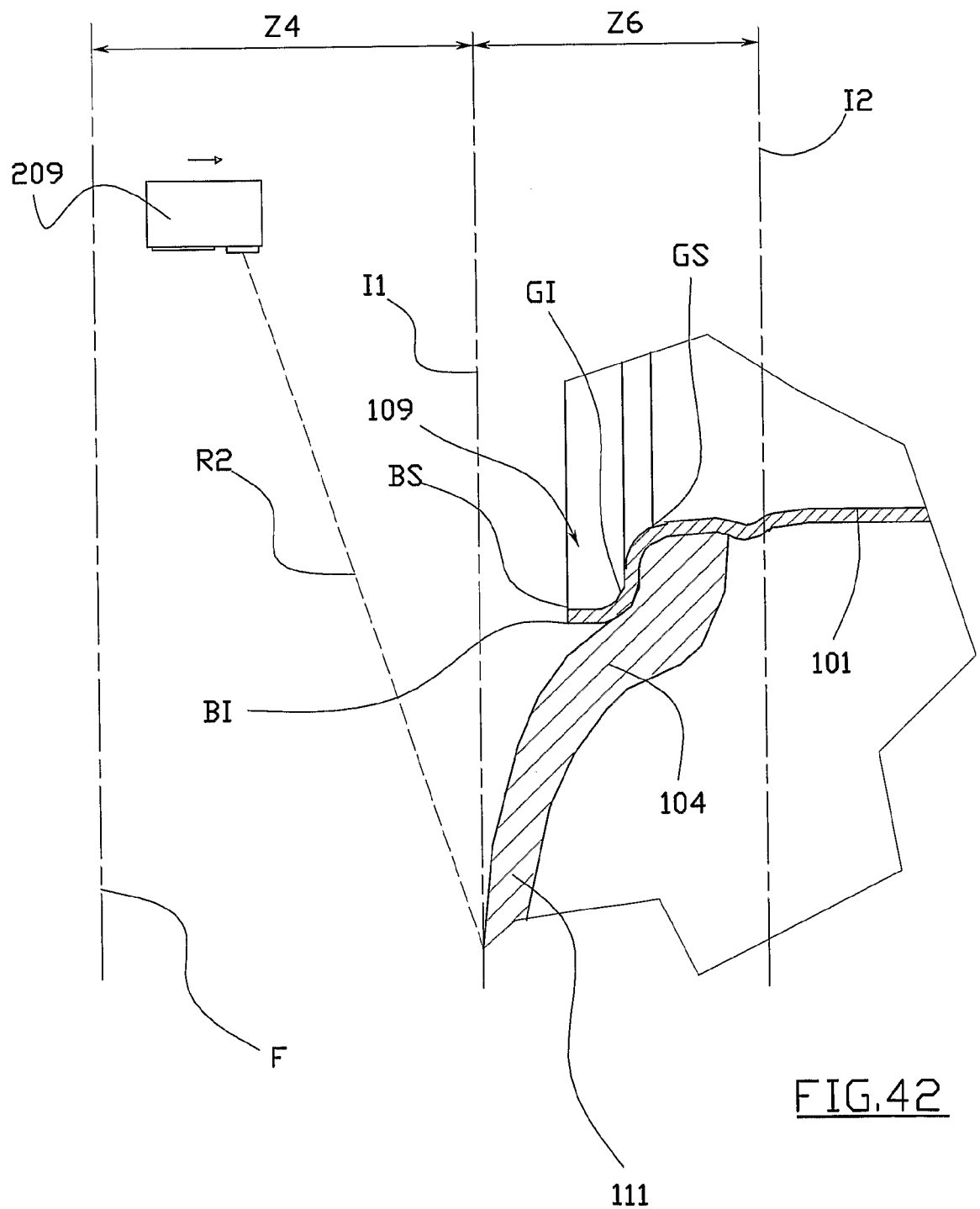

Figures from 38 to 41 shown the images taken by the lateral camera 206 during some stages of an alternative functioning mode of the machine of FIG. 12;

FIG. 42 schematically illustrates the real position of the lateral pick-up device 209 at the instant shown in FIG. 38.

BEST MODE FOR CARRYING OUT THE INVENTION

The balancing machine 1 illustrated in figures from 1 to 11 comprises a fixed structure 2, or box-shaped body, from which a driven rotating shaft 3 projects, on which the wheel 100 to be balanced is coaxially fixed.

The wheel 100 comprises a hub 101 exhibiting a narrow radial portion 102, also known as the spider, which supports a substantially channel-shaped cylindrical portion 103, which is the part the term "rim" is usually specifically applied to, on which a tyre 104 is mounted.

The spider 102 is provided with a central hole 105 by which the wheel 100 is positioned on the vehicle.

Figure 1:
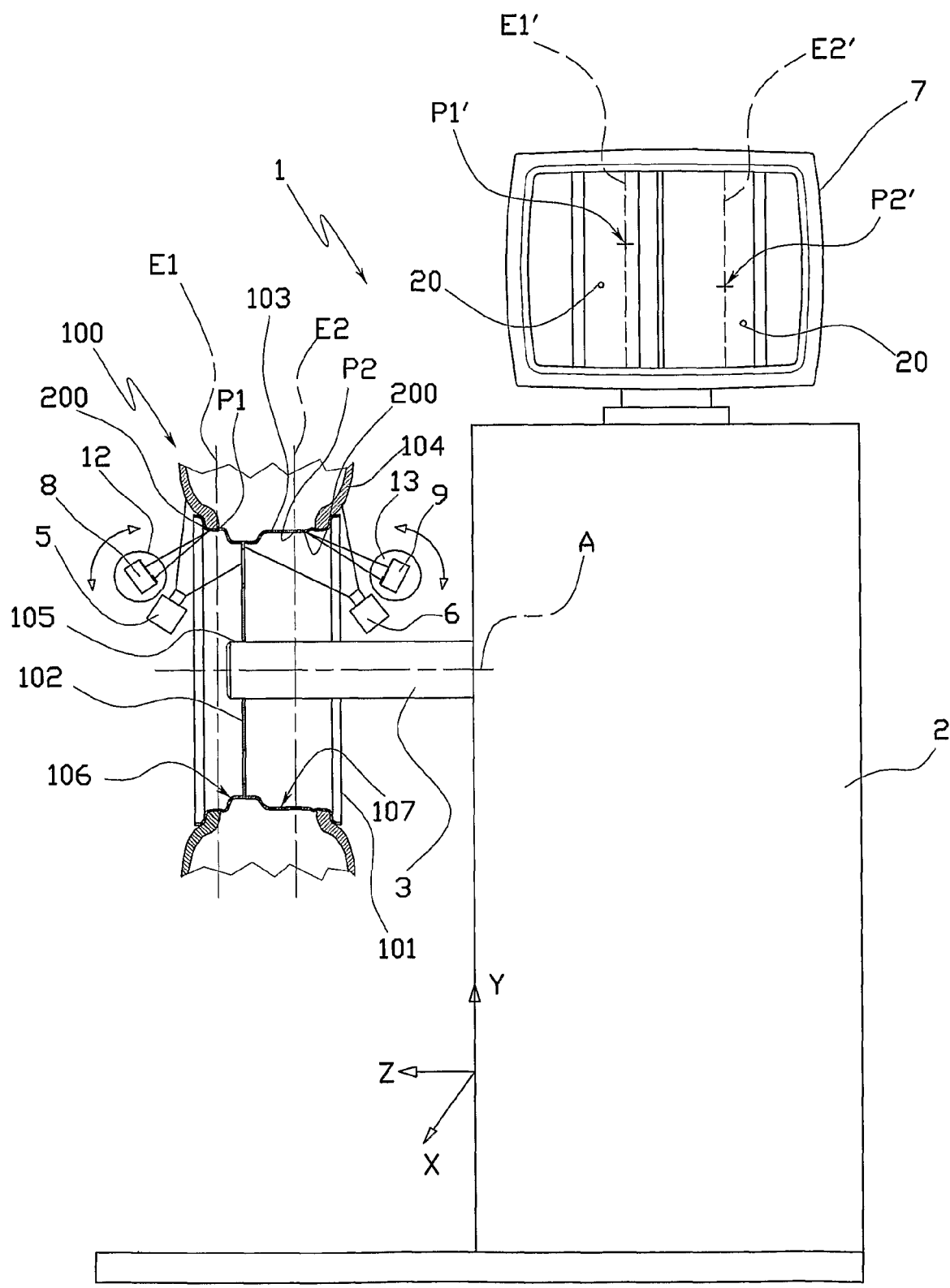
FIG. 1 illustrates a machine for balancing vehicle wheels according to the invention.

As illustrated in FIG. 1, the spider 102 sub-divides the internal surface of the hub 101 channel into a front part 106 and a back part 107, of which the front part 106 is destined to face outwards when the wheel 100 is mounted on the vehicle.

The wheel 100 is fixed on the balancing machine 1 by threading the central hole 105 of the hub onto the projecting part of the rotating shaft 3, which shaft 3 is provided with usual blocking means (not shown) which centre the wheel 100 on the shaft 3 and make them solid to one another.

The rotating shaft 3 belongs to a measuring group (not shown as of known type) which group comprises special force transducing devices for measuring the imbalance of the wheel 100 when the wheel 100 is set in rotation by the shaft 3.

Figure 2:
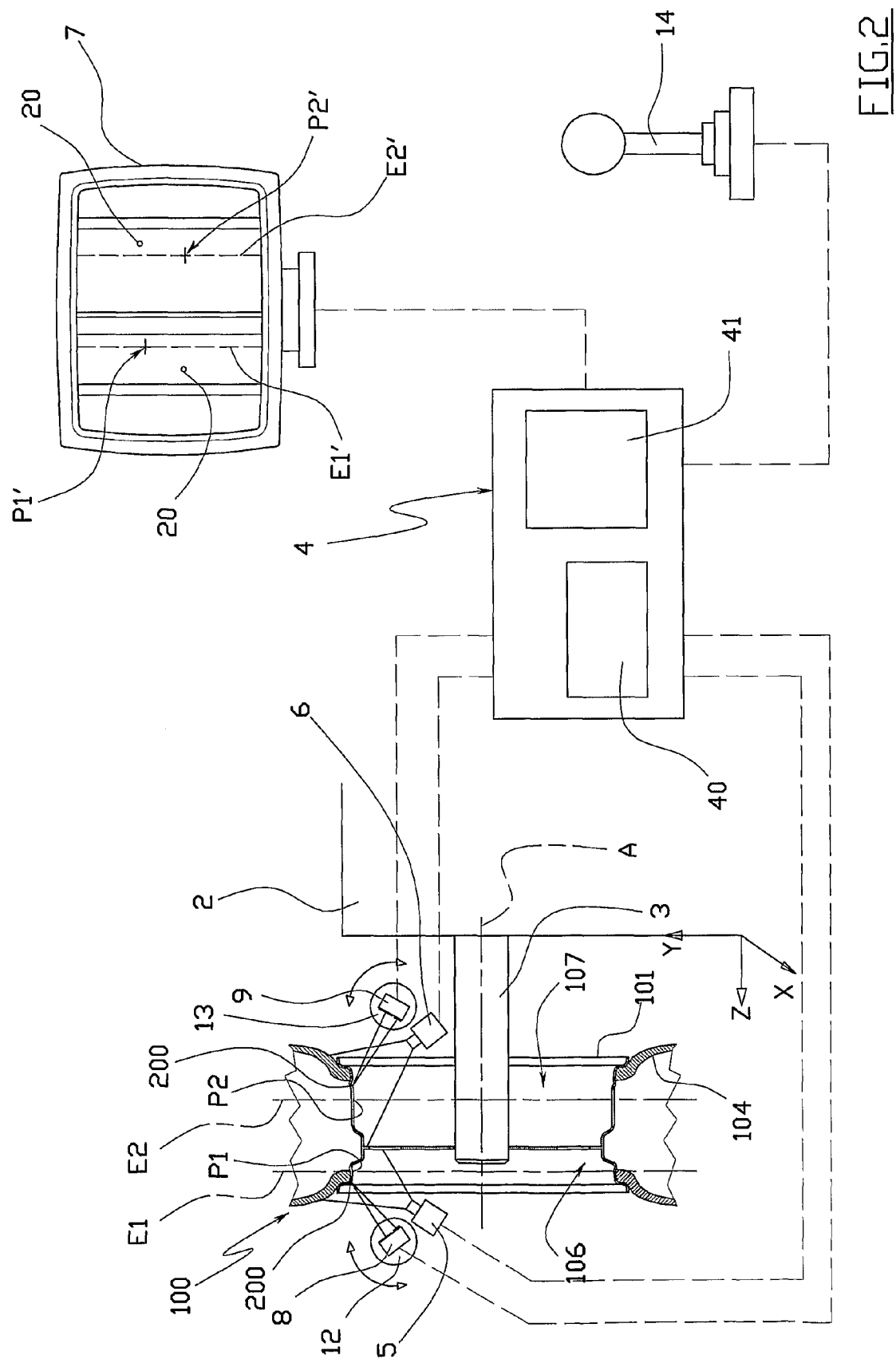
FIG. 2 is a functional diagram of the machine illustrated in FIG. 1.

The transducer devices are connected to the electronic calculator 4, illustrated schematically in FIG. 2, which comprises, among other things, a central memory 40 and a data processing unit 41 such as a computer.

In this way, the values measured by the transducer devices are transmitted to the electronic calculator 4 which, on the basis of parameters which will be better explained herein below, determines the entity and the correct positioning of the weights 18 which will be fixed on the hub 101 in order to compensate for the wheel 100 imbalances.

According to the invention, the balancing machine 1 comprises two video cameras 5, 6 arranged on opposite sides of the wheel 100 mounted on the rotating shaft 3 and having their lenses facing the internal surface of the hub 101 channel.

In particular, the camera 5 frames the front part 106 of the hub 101 while the camera 6 frames the back part 107.

Each camera 5, 6 preferably frames the wheel 100 at a fixed angle, so as constantly to frame a portion of the hub 101 which is in a predetermined angular position with respect to the axis of the rotating shaft 3.

The invention advantageously comprises each camera 5, 6 being associated to relative actuator means (not illustrated as of known type) which vary the camera position and/or the angle thereof, for example in order to adapt it to various types of workable wheels.

As is schematically illustrated in FIG. 2, the cameras 5, 6 are connected to the electronic calculator 4, which instantaneously projects the images taken onto a screen 7.

In the illustrated example, the screen 7 is a monitor which is located on the balancing machine 1 in a suitable position to be easily observed by the operative.

Note that in the figures of the drawings, for the sake of simplicity of presentation, the images taken by the cameras 5, 6 show the edges of the hub 101 as being straight.

The edges are actually curved because of the camera 5, 6 angle.

As illustrated in FIG. 1, each camera 5, 6 is associated to a pick-up device, respectively 8 and 9, which detect the spatial position of a point on the hub 101 without direct contact with the point itself.

The pick-up devices 8, 9 are quite commonly used in the sector of balancing machines, and are usually optical devices for distance measuring.

Figure 3:
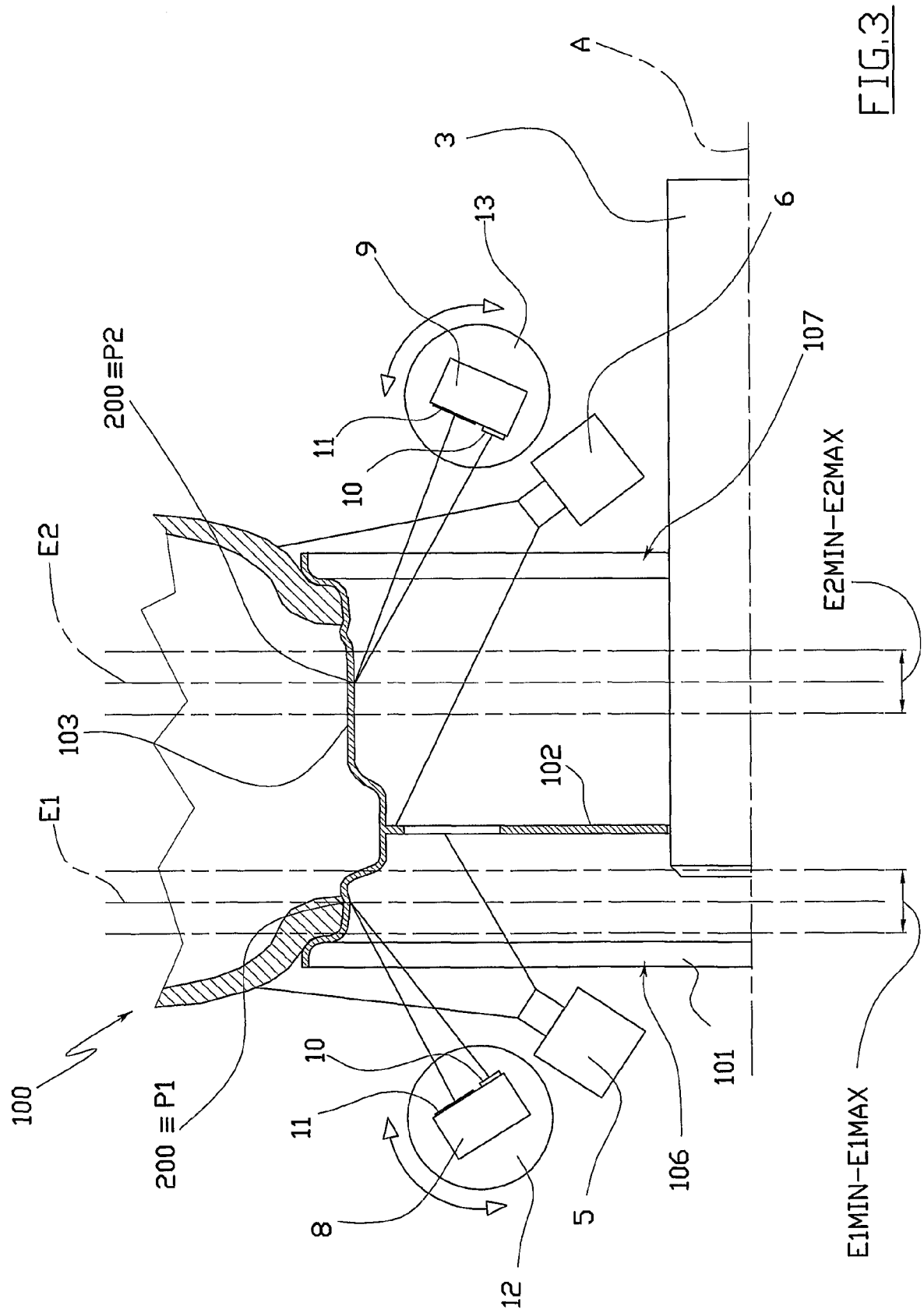
FIG. 3 is an enlarged detail of FIG. 1.

Schematically they comprise an emitter 10 of a light beam and a receiver 11, located by the side of the emitter 10 and able to receive the light beam when reflected back from a surface, so as to measure the distance separating the surface from the emitter 10 (see FIG. 3).

Generally the light beam emitted by the emitter 10 is a laser beam, capable of generating on the struck surface a light trace 200 having a rather well-defined outline.

Each pick-up device 8, 9 is associated to respective means for activating 12, 13 which move the device 8, 9 with respect to the balancing machine 1, in order to direct and/or orientate the laser beam with respect to the wheel 100. In particular, the laser beam emitted by the pick-up device 8 can strike the surfaces of the hub 101 framed by the camera 5; while the laser beam emitted by the pick-up device 9 can strike the surfaces of the hub 101 which are framed by the camera 6.

In the illustrated example, the pick-up devices 8, 9 are both mounted at a respective fixed point of the balancing machine 1, and the relative means for activating 12, 13 are destined to rotate the pick-up devices 8, 9 in the space about a perpendicular axis to the rotating shaft 3, such as to vary only the orientation of the emitted laser beam.

In particular, each pick-up device 8, 9 performs a finite run between two distinct end-run positions, such that the light trace 200 it generates can displace on the internal surface of the hub 101 along a trajectory which develops along the whole longitudinal development of the hub 101 itself. In this way, the light trace 200 can effectively strike any point of the longitudinal profile of the hub 101.

Alternatively, each means for activating 12, 13 could comprise a mobile organ, such as a mechanical arm having one or more degrees of liberty, which could translate the relative pick-up device 8, 9 with respect to the balancing machine 1, for example in a perpendicular plane to the axis A of the rotating shaft 3 and/or in a parallel direction to the axis itself.

In both cases, each movement of the pick-up devices 8, 9 is measured and transmitted to the electronic calculator 4 by special electronic devices, such as for example linear encoders and/or rotational encoders associated to the means for activating 12, 13.

On the basis of these measurements, the electronic calculator 4 can calculate and memorise, instant-by-instant, the position of the pick-up devices 8, 9 with respect to a predetermined known reference system XYZ fixed with respect to the balancing machine 1, as well as the inclination of the laser beams with respect to the same fixed reference system XYZ.

Typically, the reference system XYZ is defined by the flank of the fixed structure 2 from which the rotating shaft 3 projects, and by the rotation axis A of the rotating shaft 3 itself.

In the invention, after having fixed the wheel 100 on the rotating shaft 3, the cameras 5, 6 are activated in order to project the images of the internal surface of the hub 101 channel onto the screen 7.

By looking at the screen 7, the operative makes an arbitrary choice of two distinct balancing planes E1, E2 in the images, which planes E1, E2 are perpendicular to the wheel 100 axis, and on which two planes E1, E2 he wants to position the weights 18 on the hub 101.

The choice is made completely autonomously, on the basis of the shape and size of the hub 101, and according to the experience and preferences of the operative.

In particular, the choice is made by the operative by selecting, from the images, two points P1' and P2' at points of the hub 101 through which the respective selected balancing planes E1, E2 pass.

As only one plane which is perpendicular to the wheel 100 axis passes at each of the points on the hub 101, in this operation the operative arbitrarily and univocally selects the position of the balancing planes E1, E2.

Figure 4:
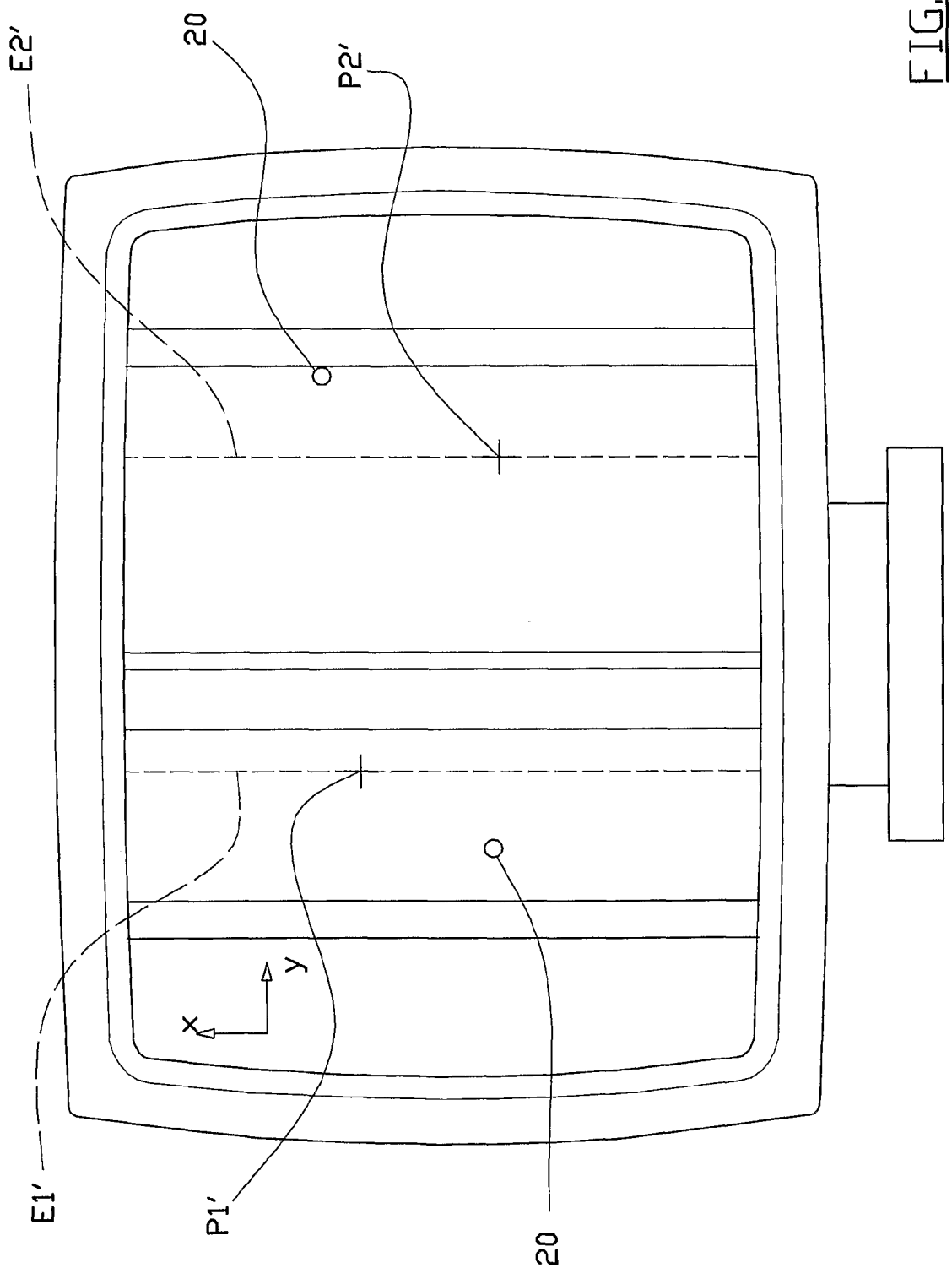
FIG. 4 is an enlarged detail of FIG. 1.

As illustrated in FIGS. 1, 2 and 4, two broken lines pass through points P1' and P2', denoted respectively by E1' and E2', which represent, on the images, the intersection lines between the internal surface of the hub 101 and the preselected balancing planes E1, E2 respectively.

The projections E1', E2' of the intersection lines, which are generated by the electronic calculator 4 onto the screen 7, will for the sake of simplicity be called the balancing planes E1, E2.

Note that although in the figures the projections E1', E2' seem to be straight, they are generally curved, like the edges of the hub 101.

After the operative has made his choice, the pick-up devices 8, 9 are commanded to move in order to bring the laser beam emitted by each of them to strike the internal surface of the hub 101 at the pre-selected balancing planes E1, E2 respectively.

In a first embodiment of the invention, this lining-up stage is done under the direct control of the operative, who acts on the means for activating 12, 13 of the pick-up devices 8, 9 using manual selectors 14, such as for example a joystick or a keyboard (see FIG. 2).

In particular, while observing the screen 7 he moves the projections 20 of the light traces 200 generated by the laser beams up to positioning them each at the projections E1' E2' of a relative balancing plane E1, E2.

In a further embodiment of the invention, the lining-up stage is done automatically under the control of the electronic calculator 4 which is directly connected to the means for activating 12, 13 of the pick-up devices 8, 9.

In this case the images taken by the cameras 5, 6 are managed by the electronic calculator 4 via a software program, which enables the operative to select points P1', P2' directly on the screen 7, at the pre-selected balancing planes E1, E2.

The selection can be done, for example, by direct contact with the screen 7, if it is a touch-screen, or can be done using a mouse pointer, an optical pen, a keyboard, a joystick or other known systems.

Once the selection has been made, the electronic calculator 4 recognises the selected points P1', P2' using the software program and automatically commands the means for activating 12, 13 of the pick-up devices 8, 9 such as to bring the laser beams to strike the hub 101 at the pre-selected balancing planes E1, E2.

In more detail, for each pre-selected point P1', P2' the program performs a tracking process of the laser trace on the images, which process comprises the operations illustrated herein below (see FIGS. 6 and 7).

Firstly, the software program acquires the coordinates of the selected point, for example P1', in a two-dimensional reference system xy which is fixed with respect to the image projected on the screen 7.

Then, using the coordinates, the process calculates, within the reference system xy, the equation of the projection E1' of the pre-selected balancing plane E1.

At this point, the program performs an operation in which it identifies, in the reference system xy, the coordinates of the projection 20 of the light trace 200 displayed on the images.

This identification stage consists in a preliminary filtering operation of the image taken by the camera 5, in order to eliminate noise and at the same time to sharpen the most marked lines in the image.

Then an analysis of the properties of the image pixels is made, such as for example an analysis of the colour or tone, in order to locate the projection of the light trace 200 of the laser beam on the image.

As the laser used is generally red or green, it has been found very advantageous to work on the red or, respectively, green component of the image.

Once the coordinates of the projection 20 of the light trace 200 in the reference system xy have been located, the electronic calculator 4 is able to calculate the distance D which on the two-dimensional image separates the projection E1' of the pre-selected balancing plane E1 from the projection 20 of the light trace 200.

Thanks to this technique, the calculator 4 can automatically pilot the means for activating 12 of the pick-up device 8, in order to position the light trace 200 at the balancing plane E1.

This stage can be done in various ways, each of which is performed by the calculator 4 using the software installed therein.

In a first way the calculator 4 performs the following cycle:
identification of the coordinates with respect to the image of the projection 20 of the light trace 200,
calculation of the distance D on the image of the projection 20 of the light trace 200 with respect to the projection E1' of the pre-selected balancing plane E1,
if the calculated distance is lower than a predetermined value (representing a sufficient closeness) the cycle is terminated, otherwise a real displacement of the pick-up device 8 is commanded, and the cycle is reset to restart from point 1.

Obviously the displacement of the pick-up device 8 must be done in such a way as to produce a nearing between the projection 20 of the light trace 200 of the laser and the projection E1' of the balancing plane E1.

This calibration can be performed with a test cycle in which, following a series of displacements in various directions of the pick-up device 8, identification is made of the direction in which a reduction of the distance D between the projection 20 of the light trace 200 and the projection E1' of the balancing plane E1 is obtained.

A second way, alternative to the above-described way, comprises the electronic calculator 4 performing a search for the smallest distance between the projection E1' of the pre-selected balancing plane E1 and the projection 20 of the light trace 200.

In this case the calculator 4 commands the pick-up device 8 to move intermittently between the first and the second endrun position, performing a series of predetermined advancing steps and stopping time-by-time.

Consequently it commands the light trace 200 to displace intermittently on the hub 101 along the longitudinal profile of the hub 101 itself.

In particular the displacement of the pick-up device 8 is done in the following way:
at each stop position the spatial position of the pick-up device 8 with respect to the fixed reference system XYZ of the balancing machine is measured and memorised, and the value D1 is calculated, being the distance D between the projection 20 of the light trace 200 and the projection E1' of the pre-selected balancing plane E1,
then the pick-device 8 is advanced by a step, up until it reaches the following stop position, where the new value D2 of the distance D between the projection 20 of the light trace 200 and the projection E1' of the pre-selected balancing plane E1 is calculated,
if the value D2 is smaller or equal to D1, this means that the projection 20 of the light trace 200 has neared (or, more precisely, has not distanced from) the projection E1' of the balancing plane E1; the pick-up device 8 is then advanced once more,
if D2 is greater than D1, this means that the projection 20 of the light trace 200 has distanced from the line E1', i.e. that D1 was the minimum distance obtainable between the projection 20 of the light trace 200 and the projection E1'; the advancing of the pick-up device 8 is then stopped.

At this point, the electronic calculator 4 returns the pick-up device 8 to the previous stop point, i.e. at the value D1 of the distance D.

Obviously the cycle is performed in the same way for the second pick-up device 9, in order to line up the light trace 200 with the pre-selected balancing plane E2.

There now follows a description of a third way of selecting points P1' P2' on the screen 7 and of performing the lining-up of the pick-up devices 8, 9 with the relative balancing planes E1, E2.

In this case too the mode of operation is described only for point P1', as the same process is performed for point P2'.

Firstly, the electronic calculator 4 acquires and memorises an image of the front part 106 of the hub 101 taken by the camera 5, when the laser beam emitted by the pick-up device 8 does not illuminate any point on the hub 101. In the following description, for the sake of simplicity the image will be called the base image.

Then the calculator 4 commands the pick-up device 8 to displace intermittently between the first and the second endrun positions, performing a series of predetermined advancing steps and stopping time-by-time.

During the advancing, the pick-up device 8 does not perform any distance measurement, but is limited to generating the light trace 200 on the hub 101, which trace 200 will consequently move progressively along the longitudinal profile of the hub 101 itself.

In particular, the light trace 200 performs the whole trajectory thereof, displacing on the hub 101 surfaces which are filmed by the camera 5.

At each stop position, the calculator 4 memorises the spatial position reached by the pick-up device 8 with respect to the reference system XYZ, and reads the coordinates of the projection 20 of the light trace 200 in the reference system xy of the images. It then signals the position from the projection 20 of the light trace 200 by generating on the above-mentioned base image a graphic element S for the detected coordinates (see FIG. 8).

In particular, the graphic element S is obtained by substituting at least a pixel of the base image which is in the detected coordinates with a pixel having at least a characteristic which visibly distinguishes it from the pixels of the base image.

This characteristic might be, for example, a colour or luminosity.

The pixel of the base image at the coordinates of the detected point is preferably substituted by a red-coloured pixel.

Thanks to this solution, when the pick-up device 8 terminates its advancement, the base image shows the front part 106 of the hub 101 and a set of indicated points S in red, which are substantially aligned along the longitudinal profile of the hub 101 itself.

This set of red points S represents the set of points from which a selection can be made.

At this point, the modified base image is displayed on the screen 7, where the operative can select the red point S which is located on the balancing plane E1 which he pre-selected.

As in the previous cases, this selection can be made using a touchscreen monitor, a mouse pointer, a keyboard, a joystick or any other known system.

Alternatively, the operative can choose a point on the image which is different from the red points, but located in proximity thereof.

In this case, the software installed in the electronic calculator 4 determines, from the set of red points, which one belongs to the projection E1 passing through the point selected by the operative, i.e. the red point closest thereto.

Once the selection has been made, as the spatial positions of the pick-up device 8 for each red point have been stored by the electronic calculator 4, the calculator 4 commands the means for activating 12 to bring the pick-up device 8 back into the position in which the laser trace 200 is at the selected red point S.

As previously mentioned, the selection of point P2' and the lining-up of the pick-up device 9 with the balancing plane E2 is performed in entirely the same way, using the camera 6.

When the lining-up stage is completed, the light trace 200 generated by the pick-up devices 8, 9 illuminate two points P1, P2 of the hub 101 which are substantially at the intersection between the hub 101 and respectively the pre-selected balancing plane E1, E2.

At this point, each pick-up device 8, 9 is commanded to measure the distance which separates it from the respective point P1, P2 of the hub 101 towards which it is pointed.

The command can be given by the operative, for example by pressing a button, or automatically by the electronic calculator 4.

The measurements of the distances are transmitted to the calculator 4, which on the basis of the position of the pick-up devices 8, 9 and the inclination of the laser beams with respect to the above-mentioned real reference system XYZ, calculates the spatial position of the pre-selected points P1, P2 of the hub 101.

In particular, it calculates the data useful for the wheel 100 balancing, which data are typically the distance of the measured points (P1 and P2) from the rotation axis of the wheel 100 and the distance of the points from a fixed reference plane of the balancing machine 1, perpendicular to the axis A of the wheel 100.

The distances of the points from the reference plane univocally determine the geometric position of the balancing planes E1, E2; while the distance of the points from the rotation axis A coincide with the eccentricity of the position of the weights 18 which will be fixed on the hub 101 at each balancing plane E1, E2.

Generally the above-mentioned reference plane coincides with the flank of the fixed structure 2 from which the rotating shaft 3 projects.

At this point the wheel 100 is set in rotation and the electronic calculator 4 determines (through the well-known relations linking the various geometric parameters and the vectors of the imbalance forces detected by the transducer devices of the measuring group) the entities M1 and M2 of the weights 18 which will have to be fixed on the hub 101 at the pre-selected balancing planes E1, E2 to balance the wheel, as well as the correct angular positions T1, T2 of the weights 18 in the respective planes E1, E2.

Normally the entities M1, M2 of the calculated weights 18 are different from the entities of the weights 18 the operative has available (a coincidence would be mere chance), which weights generally belong to a discrete set of weights having multiple values of, for example, five grams.

For this reason it is preferable for the balancing machine 1 to be provided with a system of correction which enables correction of the position of the balancing planes, following an arbitrary choice of other entities N1 and N2 of the weights 18, close to the calculated entities M1 and M2 but belonging to the range of weights which are actually available to the operative.

This choice can be made directly by the operative on the basis of his experience and preferences, and can be transmitted to the calculator 4 by a manual selection device; or it can be performed automatically by the electronic calculator 4 which, in the present case, will be provided with a rounding-up algorithm for the weights in relation to the available entities N1, N2 closest to the values calculated M1, M2, and will be compatible with the correct positioning on the hub 101.

To make this correction optimally, with the invention, for each initially-selected point P1, P2 on the hub 101, the spatial positions of a discrete set of further points on the hub 101 are acquired, which discrete set are at different distances from the reference plane of the balancing machine 1.

The points of each set are close to one another and form a frame, which we shall call, respectively, P1MIN-P1MAX and P2M1N-P2MAX, of which the relative measured point P1, P2 is the intermediate point (see FIG. 5).

The measurements of the pick-up devices 8, 9 are transmitted to the electronic calculator 4, which calculates, for each point, the distance from the reference plane of the balancing machine 1 and the distance from the rotation axis of the rotating shaft 3, in the same ways as those described herein above.

The electronic calculator 4 is preferably also able to perform an interpolation of the acquired values, in order also to predict the spatial position of the points of the frames P1MIN-P1MAX and P2M1N-P2MAX, which have not been directly measured.

Each P1MIN-P1MAX and P2M1N-P2MAX frame univocally identifies a corresponding frame of perpendicular planes to the rotating shaft 3, which we shall respectively call E1MIN-E1MAX and E2M1N-E2MAX, from among which the electronic calculator 4 can select the optimal balancing planes for positioning the new weights 18 N1, N2 on the hub 101.

The E1MIN-E1MAX and E2M1N-E2MAX frames must be in zones of the internal surface of the rim 103 where the weights can easily be located, i.e. in zones not exhibiting discontinuities which would hamper the application of the weights.

To this end, in the invention, on the basis of the position of the points of frames P1MIN-P1MAX and P2M1N-P2MAX, the calculator 4 is able to gather information relating to the shape of the hub 101 profile in the zones respectively comprised in the E1MIN-E1MAX and E2M1N-E2MAX frames.

In particular, for each of the zones the calculator 4 is able to detect the lean and/or the variation of lean of the hub 101 profile, with respect to the axis of the wheel 100, in order to evaluate whether the zone under examination is effectively suitable for application of weights 18.

With reference to FIG. 5, if the profile of the hub 101 in the zone under examination, for example at the E2M1N-E2MAX frame, exhibits a small and substantially constant lean, all the planes of the frame are considered by the electronic calculator 4 to be usable for the determination of the optimal balancing planes.

If, on the other hand, the profile of the hub 101 in the zone under examination, for example at the E1MIN-E1MAX, exhibits an excessive or excessively variable lean tract, the planes which pass through that tract, in the example E1A-E1MAX, are automatically excluded from the calculation.

At this point, the electronic calculator 4 performs a new calculation and determines (again on the basis of the relations linking the various geometric parameters with the entity of the weights 18) the optimal balancing planes from among those available, as well as the angular positions Z1, Z2 of the new weights 18 on the optimal planes.

As the weight N1, N2 of the new weights 18 is selected arbitrarily by the operative, or by the machine, in some cases the optimal planes calculated can fall without the E1MIN-E1MAX and/or E2M1N-E2MAX frames.

If this happens, the operative or the electronic calculator 4 will have to repeat the process, choosing two new weights N1 and N2 from among those available.

It can however happen that in some cases the correction of the entities of the weights 18 leads the optimal balancing planes to fall externally of the hub 101, with no possibility of applying the weights 18 to the hub 101 itself.

It can be demonstrated that this eventuality emerges especially in cases in which the imbalance of the wheel 100 is quite small, and the entities M1, M2 of the weights 18 obtained using the first calculation are therefore small.

In these cases, a small correction of the entity of the weight generally leads to a considerable increase in the relative distance between the optimal balancing planes. On the other hand, it is known that when the imbalances are small it is sufficient to perform the static balancing of the wheel 100, as dynamic balancing would only lead to very small and insignificant effects.

Advantageously, therefore, in the invention, if the distance calculated between the optimal balancing planes obtained with the second count exceeds the distance between the initially chosen balancing planes E1, E2 by an amount above a predetermined threshold value, the electronic calculator 4 signals the operator to perform only the static balancing.

A threshold value which has been seen to be suitable in the field of vehicle wheel 100 balancing is about 10% of the distance between the initially selected balancing planes E1, E2.

In the case of static balancing a single balancing plane will be chosen at which to apply a weight 18 on the hub 101; this choice will be made as described herein above.

Once the definitive entities of the weights 18 and the optimal balancing planes have been established, the balancing machine 1 must indicate to the operative the exact point on the hub 101 at which the weights 18 must be applied.

Figure 9:
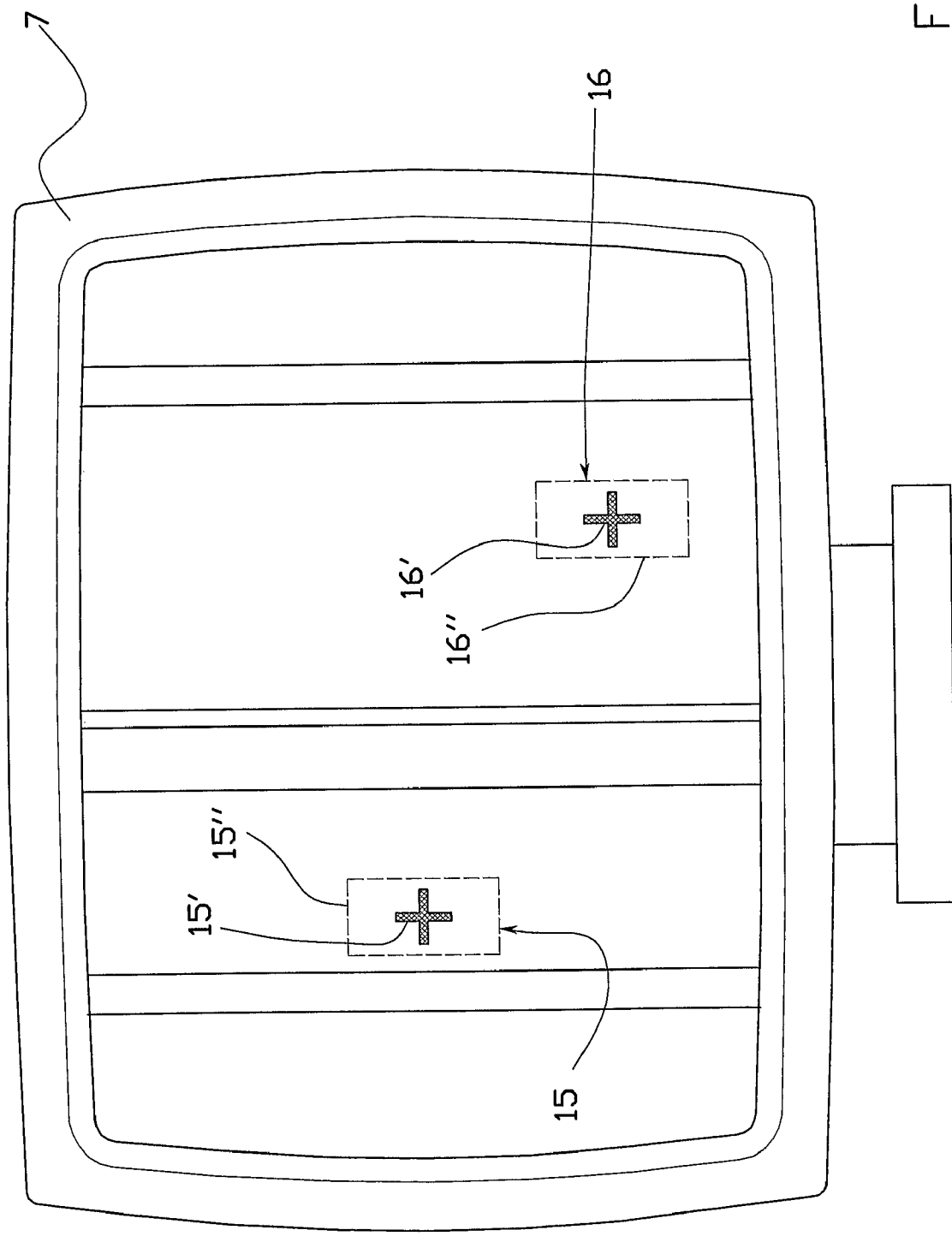
FIG. 9 is the detail of FIG. 4 during a stage of indicating the position of the weight on the wheel hub.

To this end, in the invention the electronic calculator 4 projects 7 two graphic indicators 15, 16 on the screen, which are superposed on the images taken by the cameras 5, 6 (see FIG. 9).

In particular, using a special software program, the electronic calculator 4 is able to determine the points in the image which correspond to the point on the rim of the hub in which the calculator 4 has established that the weights 18 should be applied, and is also able to position each graphic indicator 15, 16 at a respective point of the points in order to signal to the operative where to fix the weights 18.

Figure 10:
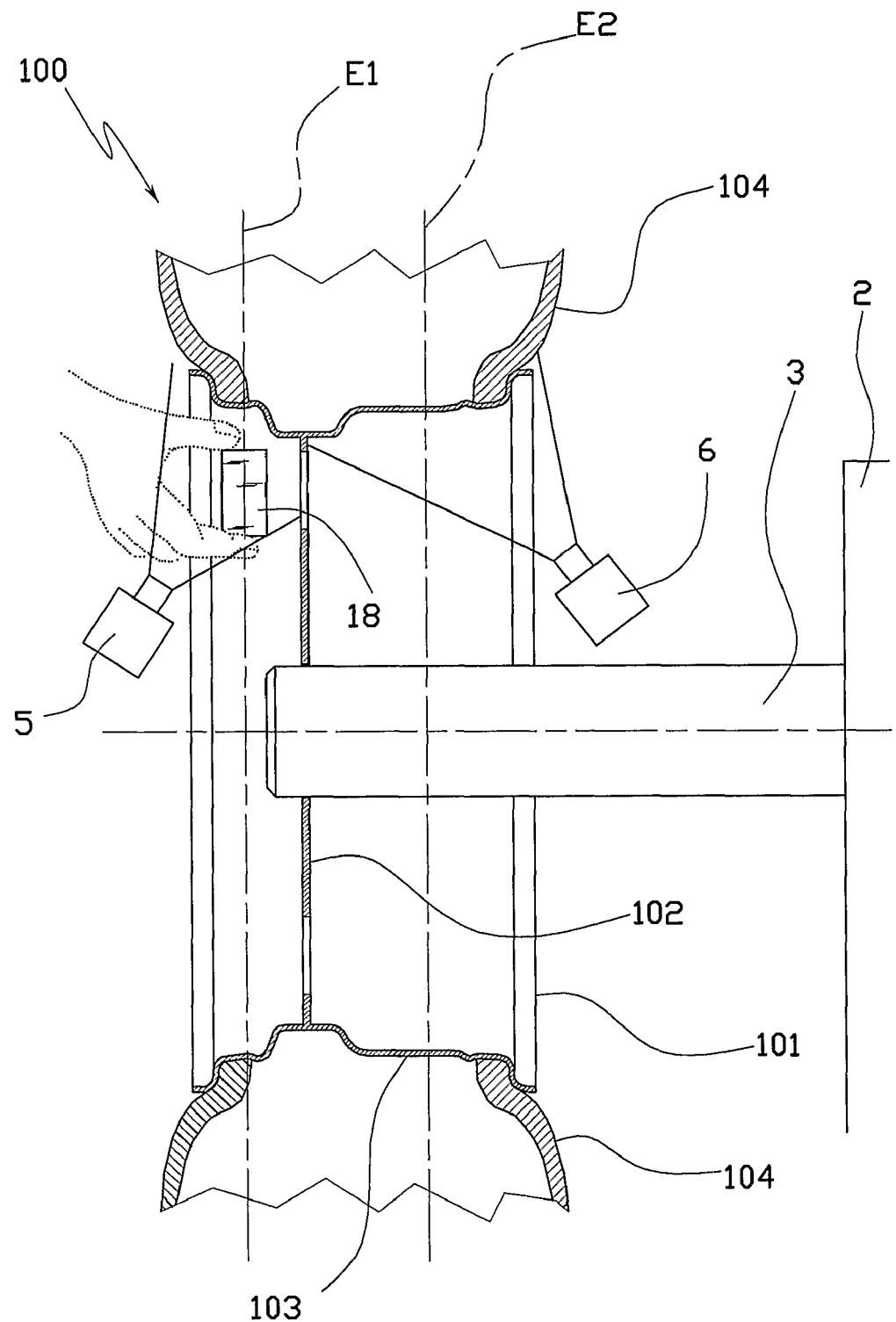
FIG. 10 is a detail of FIG. 1 during the application stage of the weight, in which some elements have been removed for the sake of clarity.
Figure 11:
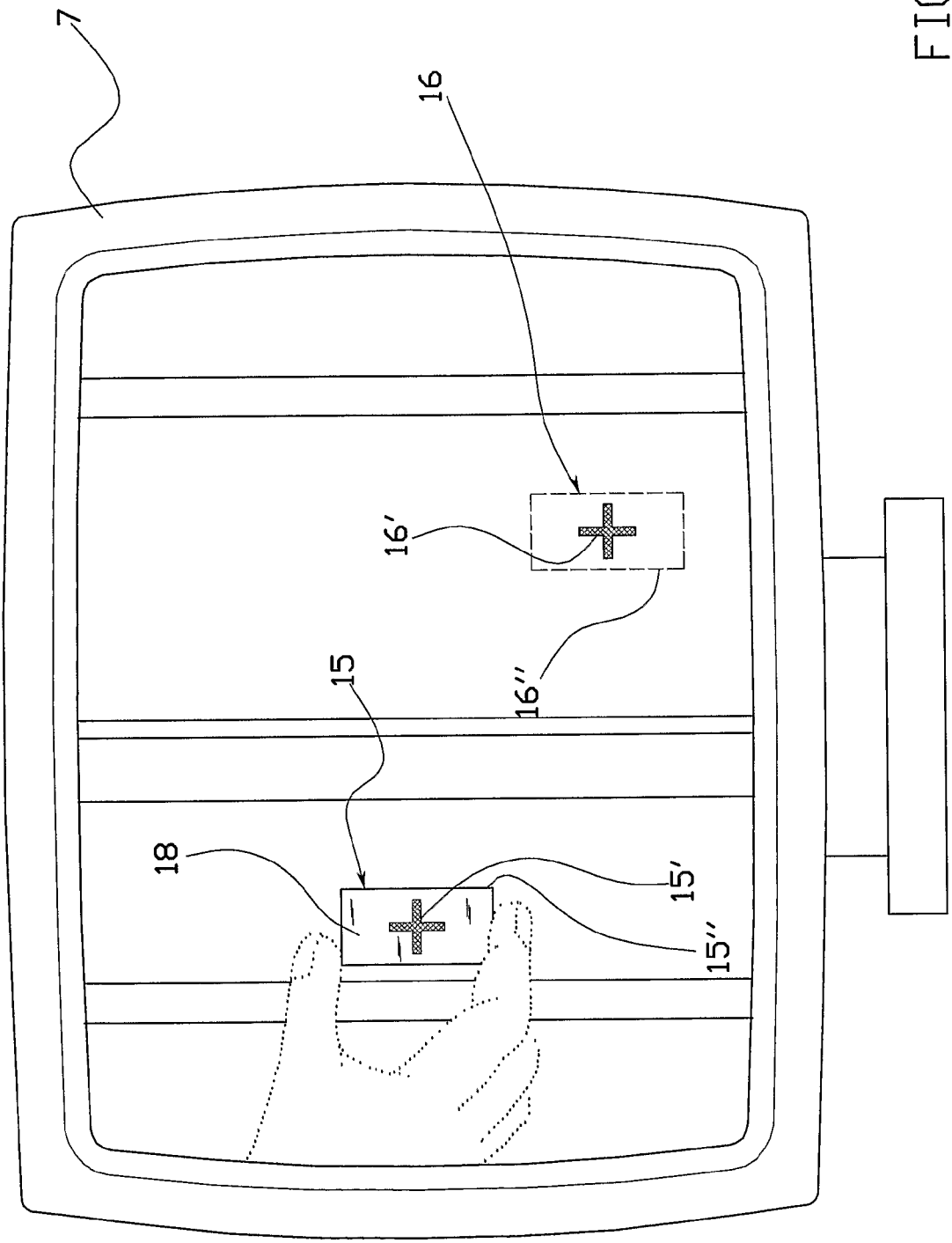
FIG. 11 is FIG. 9 during the stage of applying the weight.

Thanks to this solution, the operative can move each weight 18 internally of the channel of the hub 101, manually or using special applicator instruments (see FIG. 10); then, observing the position of the weight 18 on the screen 7, the operative can move the weight until it corresponds to the graphic indicator 15, 16 generated by the calculator 4, fixing it to the hub 101 at the correct position (see FIG. 11).

Each graphic indicator 15, 16 can comprise a pointer, either in the shape of a point or a cross, respectively 15' and 16', which precisely indicates the centre of gravity of each weight 18 on the images.

Preferably each graphic indicator 15, 16 can further comprise a closed line, respectively 15" and 16", which represents, on the images, the shape of the edge of the weight 18 to be applied.

As is understandable, the edge line 15", 16" facilitates the positioning of the weight 18 by the operative, as it provides a visible datum not only as regards the point of application, but also the size and orientation of the weight 18 on the hub 101.

Obviously the electronic calculator 4 can vary the edge line 15", 16" according to the size and shape of the weight 18 which will have to be applied time-by-time.

Since, as mentioned, the cameras 5, 6 frame a portion of the rim 103 which is in a predetermined angular position with respect to the rotating shaft 3, for each weight 18 the wheel 100 will have to be rotated on the rotating shaft 3 up until the point of real application of the weight 18 is positioned within the visual field of at least one of the cameras 5, 6.

For signalling the reaching of this condition to the operative, the invention provides various solutions.

A first solution is that the electronic calculator 4 generates the graphic indicator 15, 16 only when the point of real application enters the visual field of a camera 5, 6.

A second solution is that a fixed axis of the screen 7, for example the halfway axis, corresponds to a predefined angular position of the wheel 100 with respect to the balancing machine 1, for example 0400 hours.

In this way, it can be established that the graphic indicator 15, 16 indicates the correct point of application of the weight 18 only when it is superposed on the fixed axis of the screen 7.

A third solution is to have a brake commanded by the electronic calculator 4, which automatically blocks the rotating shaft 3 when the point of application of the weight 18 on the wheel 100 enters the visual field of the cameras 5, 6. Obviously the two graphic indicators 15, 16 described can be substituted by a single graphic indicator which selectively indicates the position of application of both the weights 18.

Finally, note that the balancing machine 1 can be provided with a further pick-up device (not illustrated) for obtaining the geometric data of the tread of the tyre of the wheel 100, such as to detect the runout measurement and transmit it to the electronic calculator 4, as will be more fully described herein below. On the basis of this measurement, and using known processing methods, the calculator 34 is able to perform further corrections on the position of the balancing planes, on the entities and on the positions of the weights, in order to optimise the wheel 100 balancing.

FIG. 12 schematically illustrates a balancing machine 201 in a further embodiment of the invention.

The balancing machine 201 comprises a fixed structure 202, from which a driven rotating shaft 203 projects, to which a wheel 100 to be balanced can be coaxially fixed.

In the illustrated embodiment, the rotating shaft 203 is a hollow bell-shaped body, the free end of which is provided with a flat circular flange, perpendicular to the rotation axis A, and a projecting centring cone 222, located coaxially to the centre of the flat flange 221.

The rotating bell 203 is rotatably coupled to a fixed central shaft 223, which is mounted on the structure 202 and projects with respect to the flat flange 221. The wheel to be balanced is mounted on the balancing machine, and orientated such that the posterior part 107 of the hub channel 101 is facing towards the support structure 202; the central hole 105 of the hub 101 is then threaded onto the projecting tract of the fixed shaft 223, and coupled with the centring cone 22, bringing the spider 102 of the wheel 100 into contact with the flat flange 221.

Finally, the wheel 100 is fixed to the rotating shaft 203 by means of a special blocking nut 224, which is screwed onto the projecting part of the fixed shaft 223.

The rotating bell 203 belongs to a measuring group (not illustrated as of known type) which comprises special force transducers for measuring the wheel 100 imbalance when the wheel 100 is set in rotation about the central axis A thereof.

The transducer devices are connected to an electronic calculator 204, illustrated only schematically in FIG. 12, which determines the entity and correct position of the weights which will be fixed on the hub 101 to compensate for the wheel 100 imbalance.

The balancing machine 201 comprises two cameras, a posterior camera 205 positioned such as to frame the tread 108 of the tyre 104, and a lateral camera 206, interposed between the wheel 100 to be balanced and the fixed structure 202 of the machine 201, which lateral camera 206 is positioned such as to frame the internal surface of the rim channel 103 of the hub 101.

In particular, the posterior camera 205 frames a portion of the tread 108 over the whole width of the tyre 104, while the lateral camera 206 frames a portion of the posterior part 107 of the channel of the rim 101 over the whole longitudinal development thereof.

In the illustrated example, the posterior camera 205 and the lateral camera 206 are located in fixed positions; however, they could be associated to means for activating for moving them with respect to the balancing machine 201, such as to vary their position and/or their angle according to the dimensions of the wheel 100 to be balanced.

As is schematically illustrated in FIG. 12, both the cameras 205, 206 are connected to the electronic calculator 204, which instantaneously projects the images taken by the posterior camera 205 on a first monitor 207A, and the images taken by the lateral camera 206 on a second monitor 207B.

Obviously, the electronic calculator 204 could project the images taken by the posterior camera 205 and the lateral camera 206 onto a single monitor, alternating them selectively or displaying them contemporaneously in two different windows.

As illustrated in FIG. 12, the posterior camera 205 is substantially directed towards the centre of the tread 108 so that the edges of the tyre 104 are practically straight in the images displayed on the monitor 207A. The lateral camera 206 is angled with respect to the wheel 100, so that the circular edges of the internal surface of the hub 101 are curved in the images displayed on the monitor 207B.

Not that the posterior camera 205 is an optional component of the balancing machine 201, in the sense that there are some functioning modes of the balancing machine 201 which do not require the presence of the posterior camera 205, and which will be described in more detail herein below.

The balancing machine 201 further comprises two optical pick-up devices for measuring the distances, respectively posterior 208 and lateral 209 pick-up devices, of the same type as the pick-up devices 8, 9 described in the first embodiment of the invention.

In particular, each pickup device 208, 209 emits a light beam directed towards a point on the surface to be measured, and receives the portion of light reflected from the surface, such as to measure the distance of the point struck.

The light beam is preferably a laser beam, which generates a visible light trace at the point struck.

The posterior pick-up device 208 is positioned at a distance from the axis A of the rotating bell 203 which is greater than the radius of the largest wheel 100 which can be dealt with by the balancing machine 201, so that it can measure the points on the tread 108 which are framed by the posterior camera 205.

The lateral pick-up device 209 is positioned at a distance from the axis A of the rotating bell 203 which is smaller than the radius of the smallest wheel 100 which can be dealt with by the balancing machine 201, so that it can measure the points in the channel of the hub 101 which are framed by the lateral camera 206.

Each pick-up device 208, 209 is associated to respective means for activating, which move it with respect to the balancing machine 201 such that it can direct the laser beam towards different points with respect to the tread 108 and the hub 101.

In the illustrated example, the posterior pick-up device 208 emits a laser beam R1 in a fixed direction which is preferably perpendicular to the rotation axis A of the rotating bell 203, and it is mounted on an extensible arm 212 which slides it both ways along a direction which is parallel to the rotation axis A.

The lateral pick-up device 209 is also mounted on a respective extensible arm 213 which moves it both ways along a direction which is parallel to the rotation axis A, but which emits a laser beam R2 which is inclined with respect to the rotation axis A.

The inclination of the laser beam R2 is selected to enable the lateral pick-up device 209 to operate also with very narrow wheels, where the rim channel of the hub 101 is completely occupied by the spokes and does not allow passage of the lateral pick-up device 209.

Both the extensible arms 212, 213 move the relative pick-up device 208, 209 starting from a predetermined rest position which is fixed with respect to the balancing machine 201. Further, the arms 212, 213 are activated by a respective step motor (not illustrated) and are possibly provided with linear encoders connected to the electronic calculator 204.

In this way, the displacement of the pick-up devices 208, 209 is constantly controlled and measured, so that the electronic calculator 204 can at all times know the positions thereof with respect to a predetermined known reference system XYZ which is fixed with respect to the balancing machine 201.

The reference system XYZ is defined by the rotation axis A of the rotating bell 203 and by a predetermined perpendicular reference plane F, in order to illuminate the portion of the channel of the hub 101 which is framed by the lateral camera 206.

The balancing machine 201 is further provided with a lighting device 210, which is located at the lateral pick-up device 209, such as to illuminate the portion of the rim channel of the hub 101 taken by the lateral camera 206.

The lighting device 210 preferably comprises a plurality of high-power LED lights, but could also be a different kind of lamp.

Further, the balancing machine 201 is provided with a laser projector 211, which emits a coherent light blade lying in a single plane.

Figure 14:
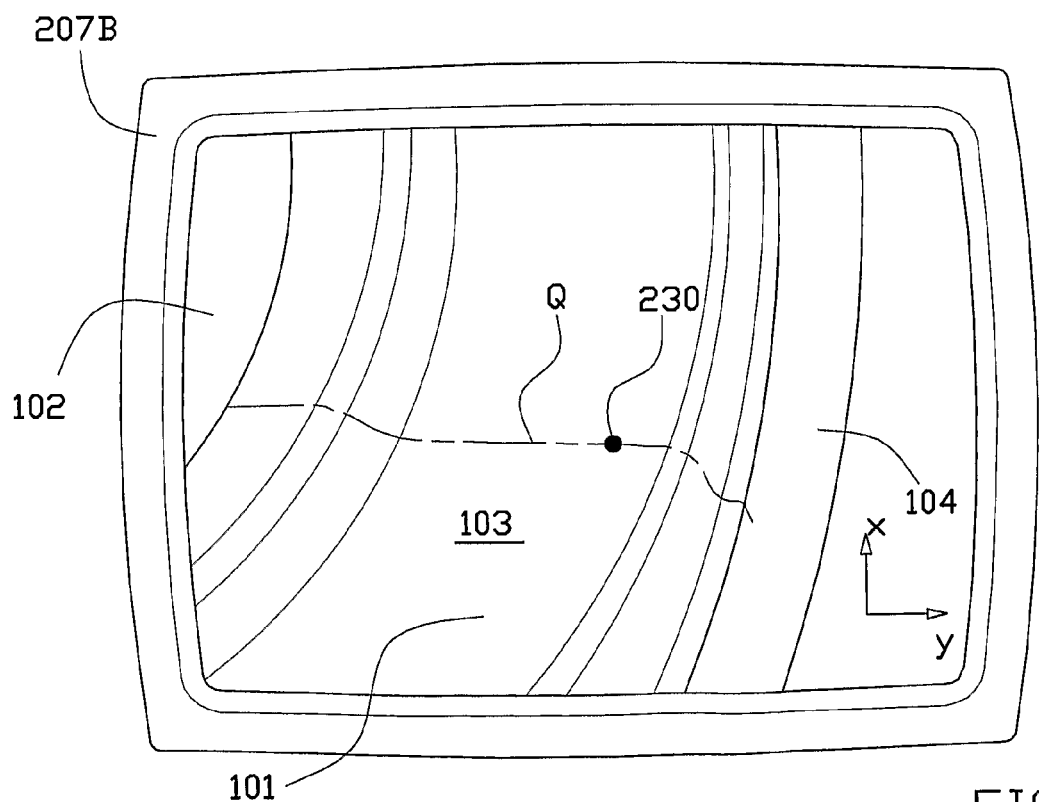

The laser projector 211 is positioned at the lateral pick-up device 209 and is oriented such that the laser blade is preferably parallel to the axis of the rotating bell 203 and strikes the portion of the channel 101 framed by the lateral camera 206, generating on the surface thereof a visible light line Q which develops in the direction of the width of the hub 101 (see FIG. 14).

In the example illustrated in the figures, the laser projector 211 is oriented such that the visible light line Q coincides with the location of the points of the hub 101 struck by the laser beam R2 emitted by the lateral pick-up device 209, when the lateral pick-up device 209 is axially displaced by the relative extensible arm 213.

In a general sense, the laser projector 211 can be oriented such that the visible light line Q does not coincide with the location of the points of the rim 101 which might be struck by the laser beam R2, and/or that the light line Q is skewed with respect to the axis of the rotating bell 203 as long as it is oriented longitudinally with respect to the wheel 100.

In the invention, after having fixed the wheel 100 on the rotating bell 203 as shown in FIG. 12, the posterior 205 and lateral 206 cameras are activated in order to display the images of respectively the tread 108 and the channel 103 of the hub 101 on the monitor 207A, 207B.

At this point, following a special command given by the user, the electronic calculator 204 automatically identifies the curve representing a predetermined circumference of the hub 101 of the wheel 100 to be balanced on the images taken by the posterior camera 206.

Figure 16:
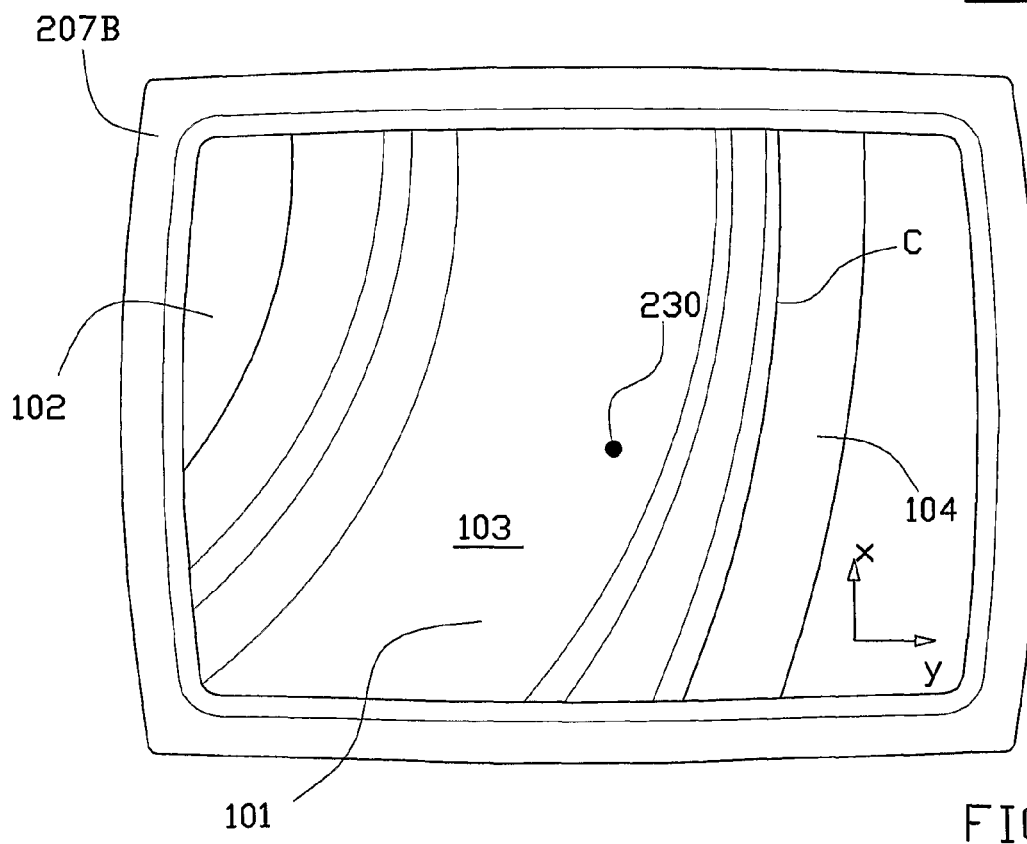

Preferably the electronic calculator 204 identifies the representative curve C of the rim edge 109 of the hub 101, i.e. the edge which is in the transition zone between the hub 101 itself and the tyre 104 (see FIG. 16).

In order to identify the representative curve C, the electronic calculator 204 subjects the images of the hub 101 taken by the lateral camera 209 to a process usually known as "edge detection", which enables and extraction from the images of a profile of the objects represented.

By way of example, in the "edge detection" process the electronic calculator 204 acquires three distinct photographs of the hub 101, in a predetermined temporal order and under different conditions.

In particular, it takes a first photograph in which the lighting device 210 and the laser projector 211 are both switched off. Then it takes a second photograph in which the lighting device 210 is switched on in order to illuminate the surface of the hub 101, while the laser projector 211 is off. Finally it takes a third photograph in which the lighting device 210 is off while the laser projector 211 is one, so as to generate the above-mentioned visible light line Q on the surface of the hub 101.

Note that alternatively to the acquiring of the third photograph, an image processed by the electronic calculator 204 could be used, as described herein above for the first embodiment.

This is in effect using a base image of the hub 101 on which the electronic calculator 204 generates a series of coloured signalling points, each of which corresponds to a respective point on the hub 101 which is struck by the laser beam R2 emitted by the lateral pick-up device 209 during an advancing run. In this way, the light points generated by the electronic calculator 204 together form on the image a visible light line, substantially the same as the visible light line Q generated by the laser projector 211.

All of the above photographs are preferably taken with minimum gain and exposure.

At this point, the electronic calculator 204 performs a process which determines, in the photographs, the zone of transition between the metal of the hub 101 rim and the rubber of the tyre 104, in order correctly to identify the curve C representing the rim edge 109 of the hub 101.

Figure 15:
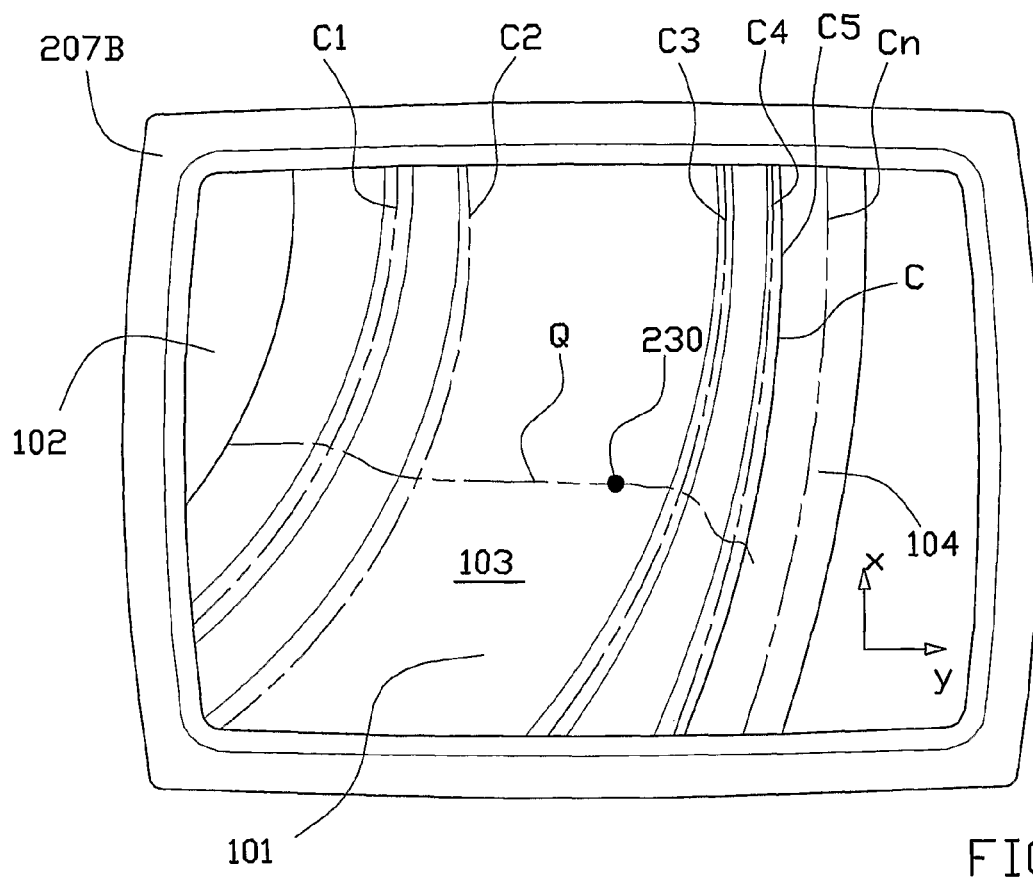

The process comprises a first analytical stage during which a plurality of curves C1-Cn of the hub 101 are identified in the photographs, all of which could be the desired curve C (see FIG. 15); the process also comprises a more refined analytical second stage in which from the curves C1-Cn the one which effectively represents the rim 109 of the hub 101 is selected.

The strategies applicable by the electronic calculator 207 for correctly performing the selection can be various, for example the photograph can be subjected to:

a chromatic analysis around each candidate curve C1-Cn;
an analysis of the luminance of the image around each candidate curve C1-Cn;
a chromatic analysis of the light line Q generated by the laser projector 211 or by the lateral pick-up device 209 according to the above process, around each candidate curve C1-Cn; or
a geometric analysis of the form of the light line Q generated by the laser projector 211, or by the lateral pick-up device 209 according to the above process, around each candidate curve C1-Cn.

For each of the above analyses, considered singly, the electronic calculator 204 attributes to each candidate curve a numeric value $V_{ij}$ representing the probability that the curve in question is effectively the desired curve C, where "i" indicates the type of analysis performed and "j" denotes the curve taken into consideration.

At the end of all of the analyses, the electronic calculator 204, for each candidate curve "j", derives a synthetic probability parameter $VT_j$, for example by obtaining the mean of values $V_{ij}$ obtained from the curve "j" for each analysis "i".

Finally, the electronic calculator 204 compares the synthetic parameters $VT_j$ of all the candidate curves "j" and selects the curve C which produced the highest parameter.

Figure 17:
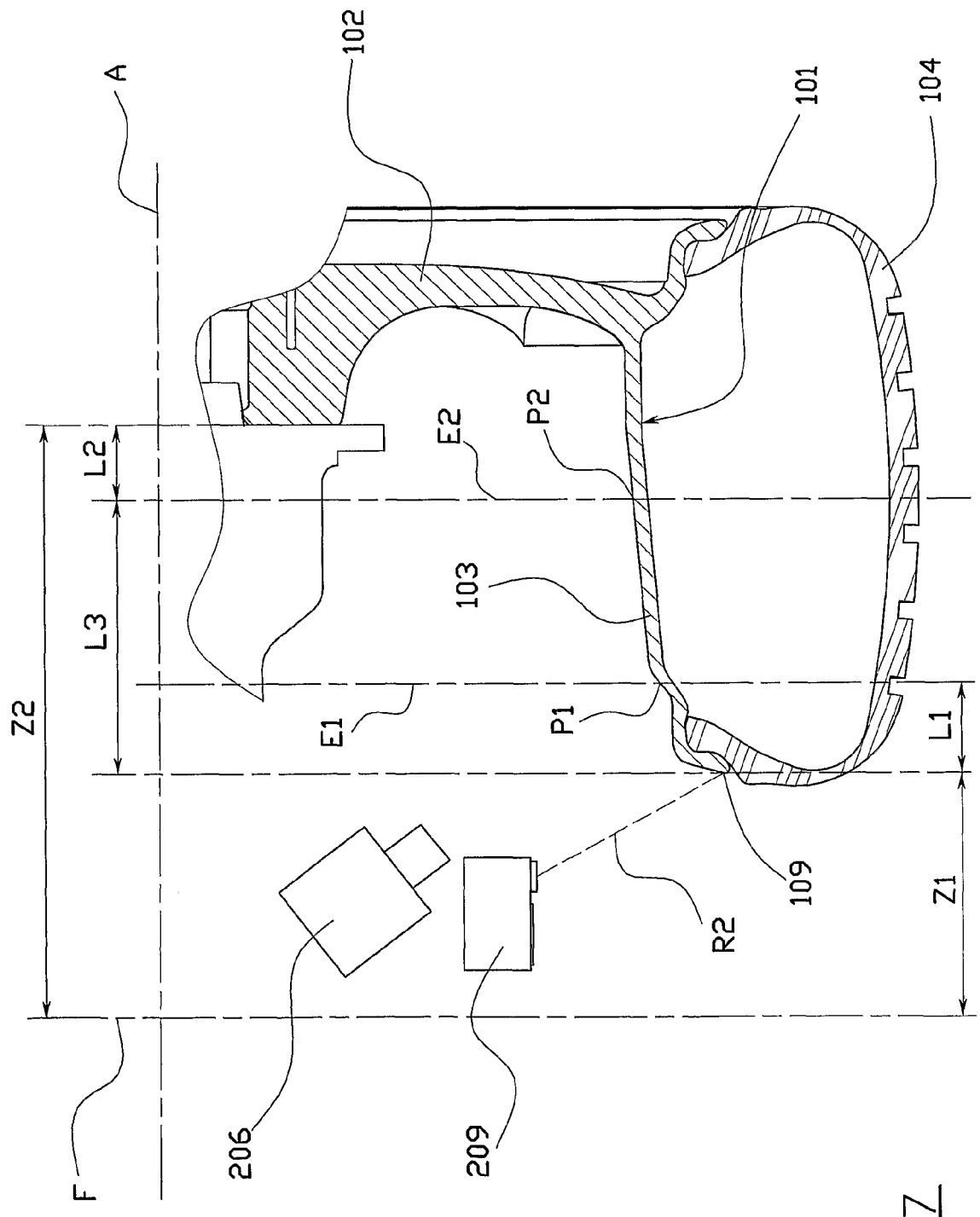
FIG. 17 shows the real position of the lateral pick-up device 209 at the moment illustrated in FIG. 16.

When the selection stage is completed, the calculator 204 commands the extensible arm 213 to displace the lateral pick-up device 209 to direct the laser beam R2 onto a point on the hub 101 which belongs to the rim edge 109 identified on the images (see FIG. 17).

This displacement is done automatically under the control of the electronic calculator 204, by means of one of the tracking processes of the light trace of the laser beam, used in the first embodiment for pointing the pick-up devices 8, 9 towards the balancing planes E1 and E2.

For example, the electronic calculator 204 calculates the equation of the curve C, previously identified, with respect to a two-dimensional fixed reference system xy of the images taken by the lateral camera 206. Then the electronic calculator 204 identifies, from the images taken by the lateral camera 206, the projection 230 of the light trace generated by the laser beam R2 on the surface of the hub 101 (see FIG. 16), and determines the coordinates of the projection 230 in the reference system xy of the images, in order to calculate the distance of the latter from the curve C. Finally, the electronic calculator 204 displaces the pick-up device 209 by a predetermined amount and repeats the preceding stages, up until the distance between the projection 230 of the laser trace and the curve C is less than a predetermined threshold value. Alternatively, the electronic calculator 204 can perform a research for the minimum value of the distances between the curve C and the projection 230 of the laser trace, as described for the first embodiment herein above.

At the end of the tracking procedure, the lateral pick-up device 209 is in a position in which the laser beam R2 is directed towards a point of the rim 109 of the hub 101, as illustrated in FIG. 17.

In this position, the lateral pick-up device 209 measures the distance separating it from the point on the hub 101, so that the calculator 204 can acquire the diameter of the rim edge 109 and the distance Z1 of the rim edge 109 from the reference plane F of the balancing machine 201.

At this point, the functioning of the balancing machine 201 includes the selection of the two balancing planes E1 and E2 of the wheel 100, at which the weights will be positioned on the hub 101.

This selection is preferably done automatically by the electronic calculator 204 according to a predetermined logic which is installed in the electronic calculator 204 during the programming stage.

In particular, the first balancing plane E1 is chosen by arbitrarily setting the distance L1 which separates it from the rim 109 of the hub 101.

The distance L1 is preferably about 10 mm towards the spider 102, which derives from the statistical fact that the channel 103 of the hub 101 of any wheel exhibits, at about 10 mm from the rim 109 thereof, a sufficiently regular surface for receiving a weight.

The second balancing plane E2 is chosen by arbitrarily fixing the distance separating it from a predetermined plane of the balancing machine 201 which is perpendicular to the axis A of the rotating bell 203, in the example by arbitrarily fixing the distance L2 which separates it from the plane of the flange 221 of the rotating bell 203 itself.

The distance L2 is preferably chosen at about 20 mm towards the rim edge 109, as statistically the channel 103 of the hub 101 of any wheel exhibits, at about 20 mm from the contact wall with the flange 221, a sufficiently regular surface to receive a weight.

Note that the choice of using the plane of the flange 221 as a reference for selecting the second balancing plane E2 is dictated by the fact that the distance Z2 of the flange 221 plane from the reference plane F of the balancing machine 201 is already known.

In this way, the electronic calculator 204 ca calculate the distance L3 which separates the rim edge 109 of the hub 101 from the second balancing plane E2, using the simple relation L3=Z2−L2−Z1.

At this point, the electronic calculator 204 displaces the lateral pick-up device 209 in a parallel direction to the axis A of the wheel 100, from the initial position in which the laser beam R2 is pointed to the rim 109 of the rim 101, towards a first operative position in which the laser beam R2 is directed at a point P1 of the channel of the hub 101 belonging to the first balancing plane E1 (see FIG. 18).

As however the laser beam R2 is inclined with respect to the advancement direction of the lateral pick-up device 209, and the diameter of the hub 101 channel is variable in the axial direction, in order to direct the laser beam R2 onto the point P1 it is not sufficient to displace the lateral pick-up device 209 by a quantity equal to L1; it is necessary for the electronic calculator 204 to perform the procedure illustrated herein below with the help of FIG. 20.

Starting from the initial position, the lateral pick-up device 209 is displaced in an axial direction by a quantity equal to L1, distancing from the reference plane F, in order to reach a new stop position. In the stop position, the laser beam R2 generally strikes a point S of the hub 101 which does not belong to the pre-selected balancing plane E1. The lateral pick-up device 209 is then commanded to measure the distance of the point S, enabling the electronic calculator 204 to acquire the distance Zs which separates the point S from the reference plane F of the balancing machine 201, and then to calculate the distance Ls which separates the point S from the pre-selected balancing plane E1, using the simple relation Ls=Z1+L1−Zs.

At this point, the lateral pick-up device 209 is newly advanced from the stop position by the quantity calculated Ls and the above-described stages are recurrently repeated up until the distance Ls is less than a pre-determined threshold value.

Once this procedure has been completed, the laser beam R2 is directed at point P1 on the hub 101 (see FIG. 18), so that the lateral pick-up device 209 detects the distance of the point P1 and the electronic calculator 204 acquires the diameter of the channel of the hub 101 at the balancing plane E1 and possibly also controls the distance thereof from the reference plane F.

Once the data relating to the first balancing plane E1 has been acquired, the lateral pick-up device 209 is displaced into a second operating position, in which the laser beam R2 is directed towards a point P2 in the hub channel 101 belonging to the second balancing plane E2 (see FIG. 19).

This displacement is done in an entirely similar way to what is described for the first balancing plane E1, returning the lateral pick-up device 209 into the initial position in which the laser beam R2 is pointed at the edge 109 of the hub 101, and using the calculated value L3 as an initial advancement (see FIG. 17).

Obviously the lateral pick-up device 209 could be displaced starting from the first operative position reached, using the difference between the value of L3 and L1 as an initial advancement value.

After having reached the second operative position, the lateral pick-up device 209 measures the distance of point P2, in order that the electronic calculator 204 can acquire the diameter of the channel of the hub 101 at the balancing plane E2, and possibly also control the distance thereof from the reference plane F of the balancing machine 201.

At the same time, the posterior pick-up device 208 is used to automatically identify the lateral flanks, external 110 and internal 111, of the tyre 104 of the wheel 100, by calculating the distances Z3 and Z4 which separate them from the reference plane F of the balancing machine 201.

As illustrated in FIG. 21, as the posterior pick-up device 208 directs the laser beam R1 in a perpendicular direction to the rotation axis A of the wheel 100, when the laser beam R1 is external of the tyre 104, the posterior pick-up device 208 (denoted by a continuous line) measures a very high distance, even out of limits; conversely, when the laser beam R1 intercepts the tyre 104, the posterior pick-up device 208 (denoted by a broken line) measures a distance which is below a predetermined threshold value.

In order to identify each lateral flank 110 and 111, the posterior pick-up device 208 advances parallel to the rotation axis A, during which run the posterior pick-up device 208 takes a successive series of samples.

For each sampling the distance measured by the pick-up device 208 is compared with a predetermined threshold device, which is fixed and stored in the electronic calculator 204 during the programming stage thereof.

If, during the advancing of the posterior pick-up device 208, the difference between the measured value and the threshold value changes significantly, this means that the posterior pick-up device 208 is in the transition zone between the tyre 104 and the empty space, i.e. that the laser beam R1 is substantially tangential to a lateral flank 110, 111 of the tyre 104 itself.

When this condition obtains, the posterior pick-up device 208 is stopped so that the electronic calculator 204 can acquire the distance of the lateral flank 110, 111 from the reference plane F of the balancing machine 201.

Figure 22:
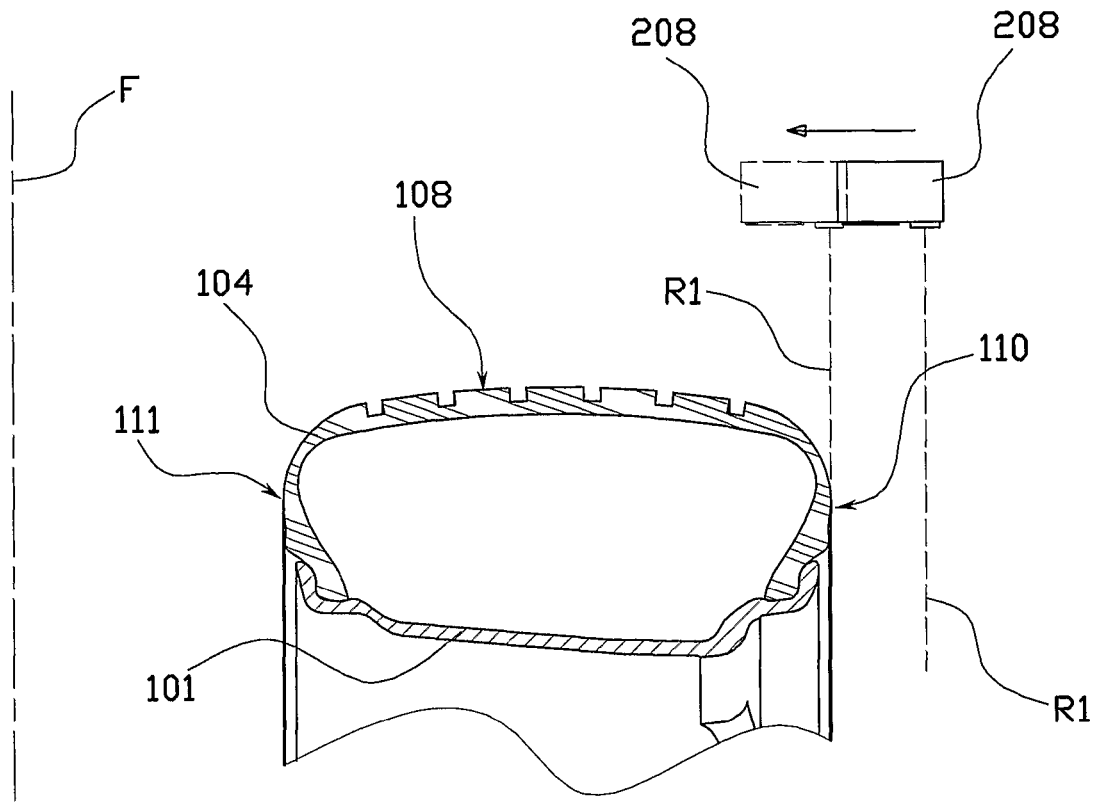

In more detail (see FIG. 22), in order to locate the external lateral flank 110, the posterior pick-up device 208 is initially located at a position (denoted with a continuous line) in which the laser beam R1 is external of the tyre 104, on the opposite side with respect to the fixed structure 202 of the balancing machine 201. Then, the posterior pick-up device 208 is progressively neared to the fixed structure 202, up until it reaches the position (denoted by the broken line) in which the distance measured during the sampling falls below the threshold value for the first time.

Figure 23:
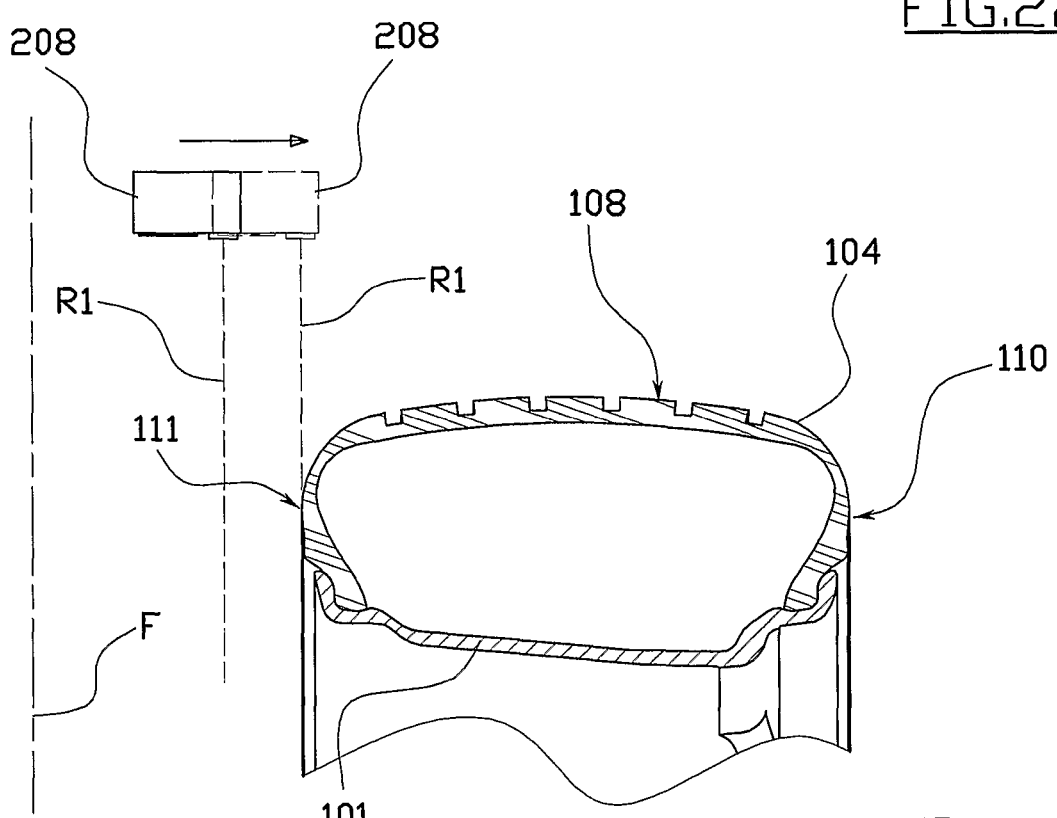

To locate the internal lateral flank 111 (see FIG. 23), the posterior pick-up device 208 is initially located in a position (denoted by a continuous line) in which the laser beam R1 is directed into the space interposed between the tyre 104 and the flank F of the support structure 202. Then the posterior pick-up device 208 is progressively distanced from the support structure 202 up until it reaches the position (denoted by the broken line) in which the distance measured during the sampling drops for the first time below the threshold value.

Figure 24:
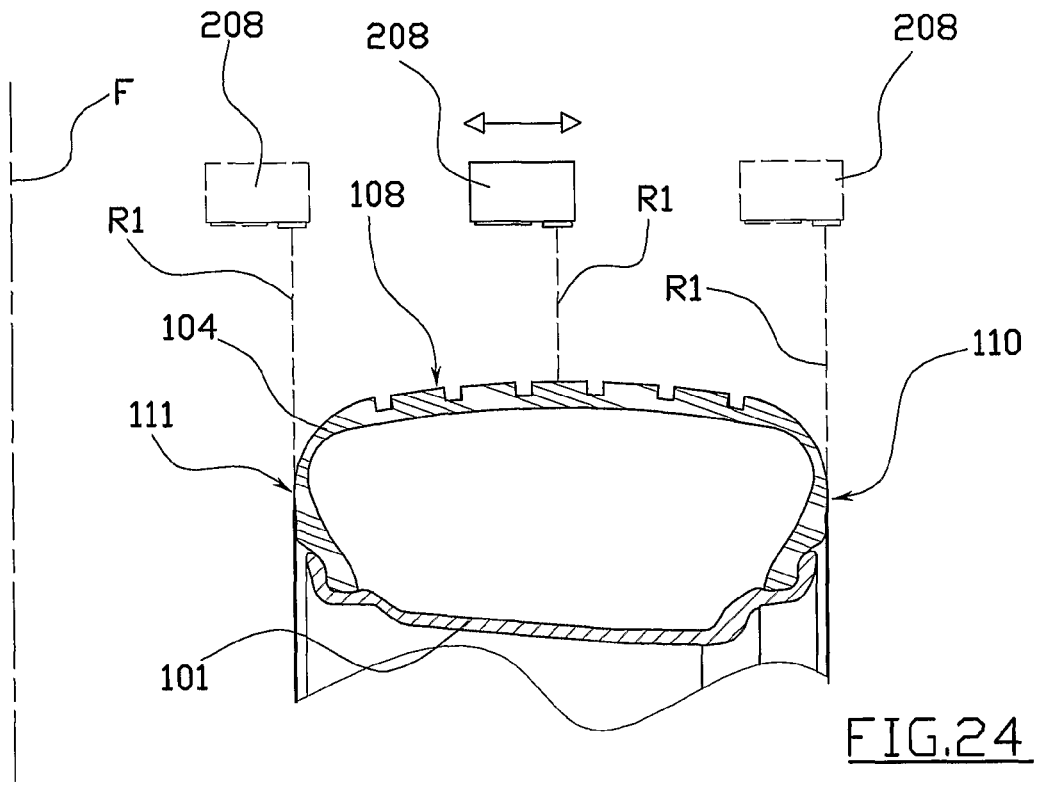

Alternatively (see FIG. 24), in order to locate both the lateral flanks 110 and 111, the posterior pick-up device 208 might be initially located in a position (denoted by a continuous line) in which the laser beam R1 is directed towards an internal point of the tread 108. Then the posterior pick-up device 208 can be displaced in one of the two possible directions, up until it reaches a position (denoted by a broken line) in which the distance measured during the sampling exceeds the threshold value for the first time.

In the invention, both lateral flanks 110, 111 of the tyre 104 can preferably be located with a single run of the posterior pick-up device 208.

Figure 25:
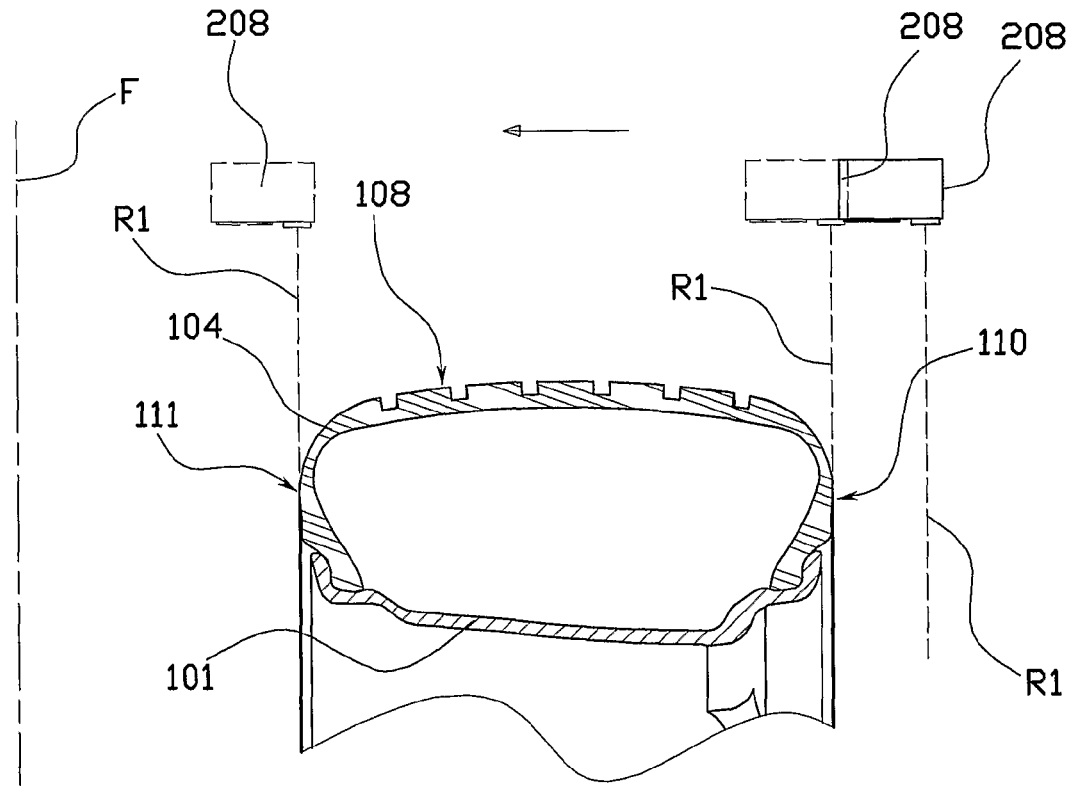
Figure 26:
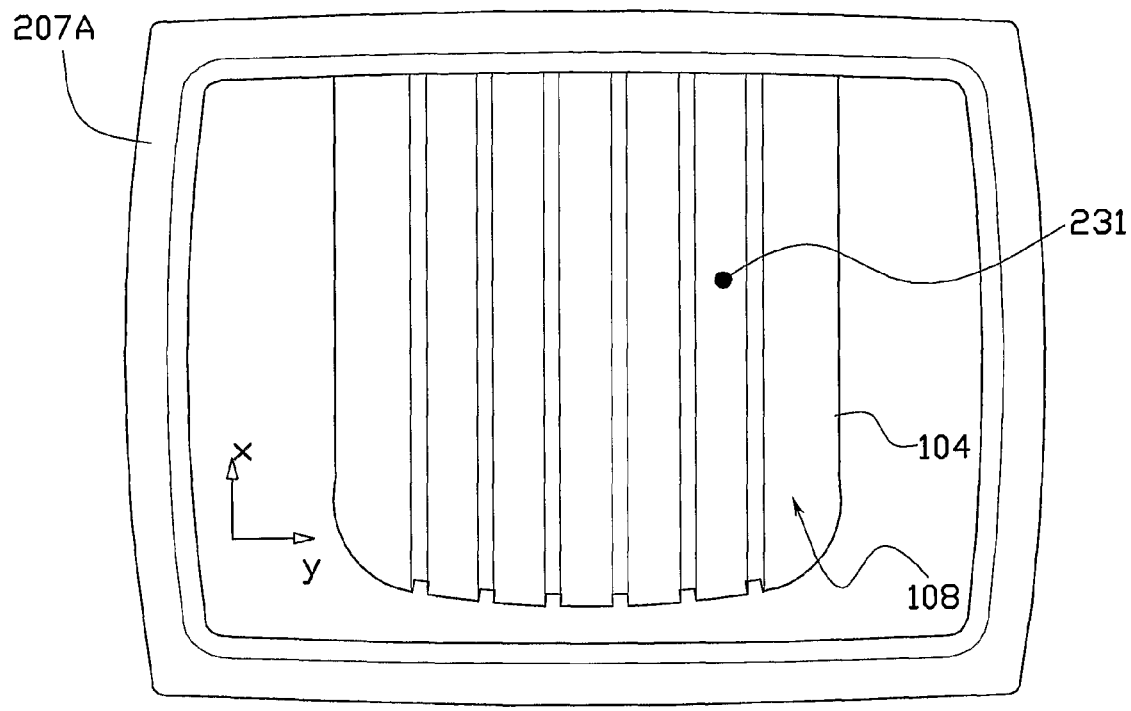
FIGS. 26, 27 and 28 illustrate the images shown by the monitor 207A during different operational stages of the machine of FIG. 1.

For example (see FIG. 25), after having located the posterior pick-up device 208 in an external position (denoted by a continuous line) of the tyre 104, on an opposite side with respect to the support structure 202, the pick-up device 208 is progressively neared to the support structure 202 up to a first position (denoted by a broken line) in which the distance measured falls for the first time below the threshold value, locating the external flank 110. Then the posterior pick-up device 208 is further neared to the support structure 202 up to a second position (denoted by a broken line) in which the measured distance newly exceeds the threshold value, locating the internal flank 111.

In the same way, the posterior pick-up device 208 could first locate the internal flank 111 and thereafter the external flank 110, with a first distancing run from the support structure 202, starting from a position in which the laser beam R1 is interposed between the flank of the support structure 202 and the wheel 100.

After having located the two lateral flanks, external 110 and internal 111, and having acquired the relative distances Z3 and Z4 from the reference plane F of the balancing machine 201, the electronic calculator 204 is able to calculate numerous parameters of the wheel 100 (see FIG. 21).

In particular, it is able to calculate the width H1 of the tyre 104 according to the relation H1=Z3−Z4; further, as the distance Z1 of the rim edge 109 of the hub 101 is known, and supposing that the wheel 100 is symmetrical, it can calculate the width H2 of the hub 101 according to the relation H2=H1−2*(Z1−Z4).

At this point, the wheel 100 is set in rotation and the electronic calculator 204 determines (using the well known relations linking the various geometric parameters and the vectors of the imbalance forces detected by the transducer groups of the measuring groups) the values of the weights which must be fixed on the hub 101 at the balancing planes E1, E2 in order to balance the wheel 100, as well as the correct angular positions of the weights in the respective planes E1, E2.

Then all the corrections relating to the balancing planes and the entities of the weights can be made, which are described herein above with reference to the first embodiment of the invention.

During these operations, the balancing machine 201 can further use the posterior and lateral pick-up devices 208 and 209 to perform a radial runout measurement on the wheel 100, i.e. the amount by which the wheel 100 profile is out with respect to a perfect circumference.

In particular, the posterior pick-up device 208 performs the radial runout measurement on the tyre 104, while the lateral pick-up device 209 performs the measurement of the radial runout on the hub 101.

In this way, by analysing and comparing the measurements obtained by the pick-up devices 208 and 209, the electronic calculator 204 is able to process and display on the monitor much information relating to the state of the wheel (for example the geometry of the wheel, lateral conditions, state of wear of the tyre, hub quality, etc.) as well as suggesting any required operations for improving the state of the wheel (for example a wheel matching correction, i.e. the reciprocal angular position between hub and tyre).

Figure 29:
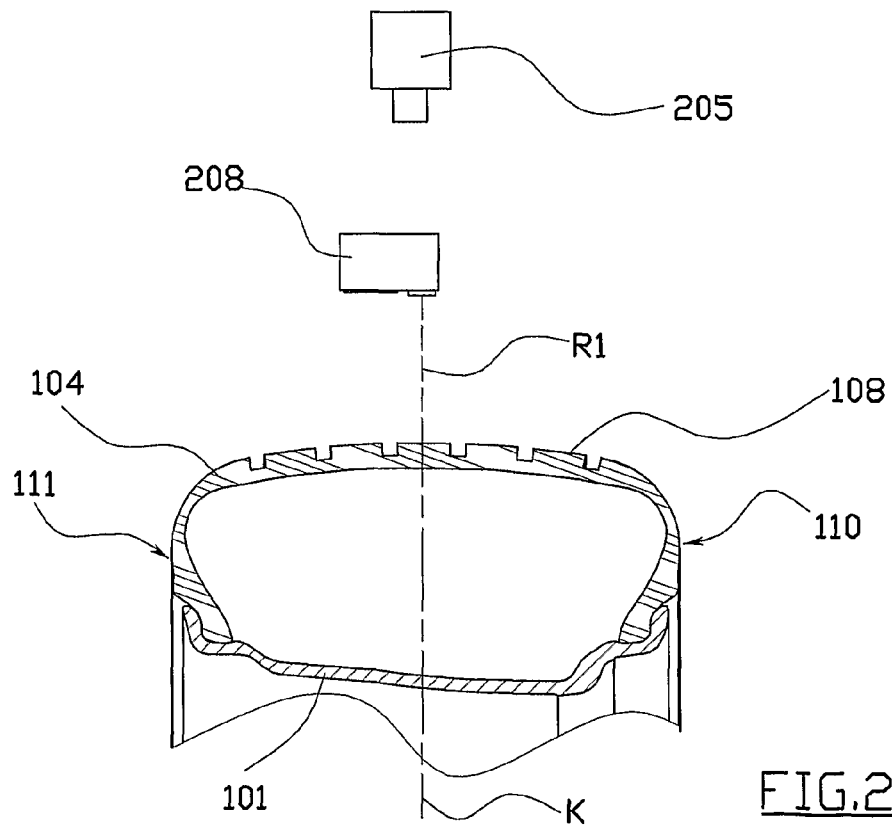
FIG. 29 shows the real position of the posterior pick-up device 208 at the instant shown in FIG. 28.
Figure 30:
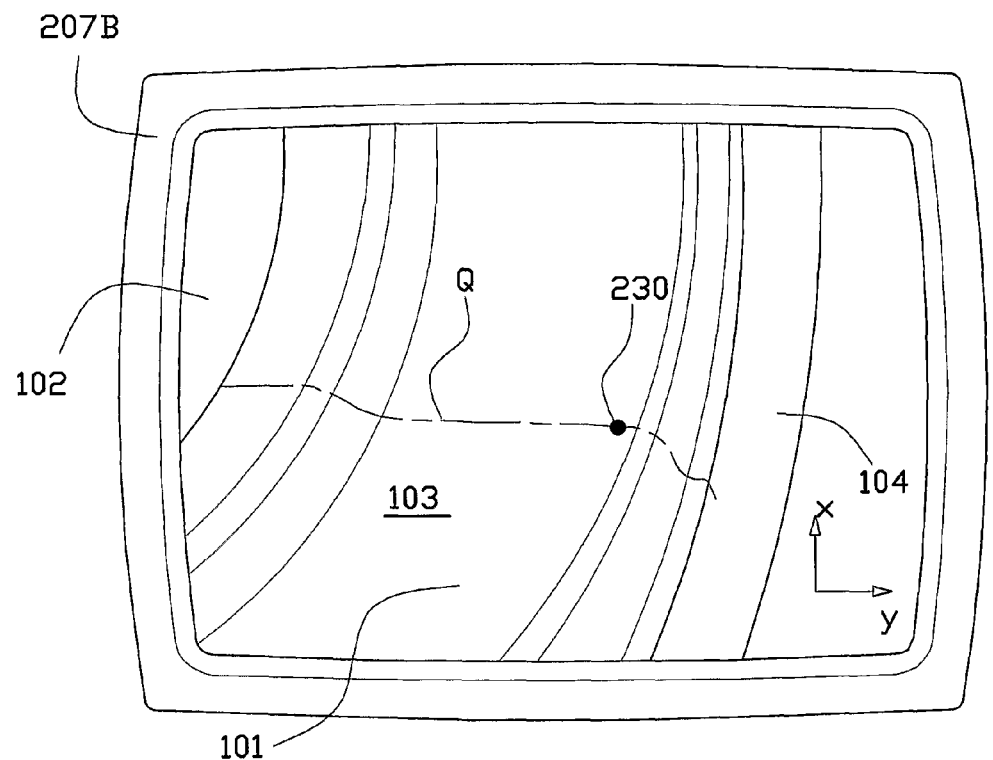
FIGS. 30, 31 and 32 show the images displayed by the monitor 207B during different operational stages of the machine of FIG. 1.
Figure 31:
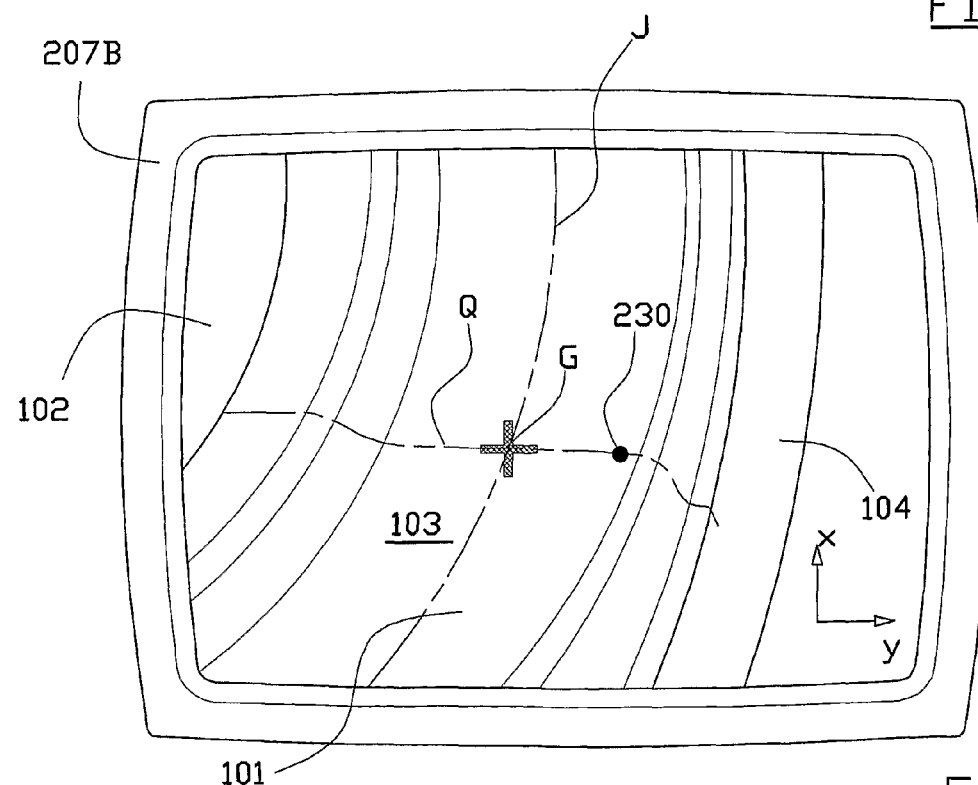
Figure 32:
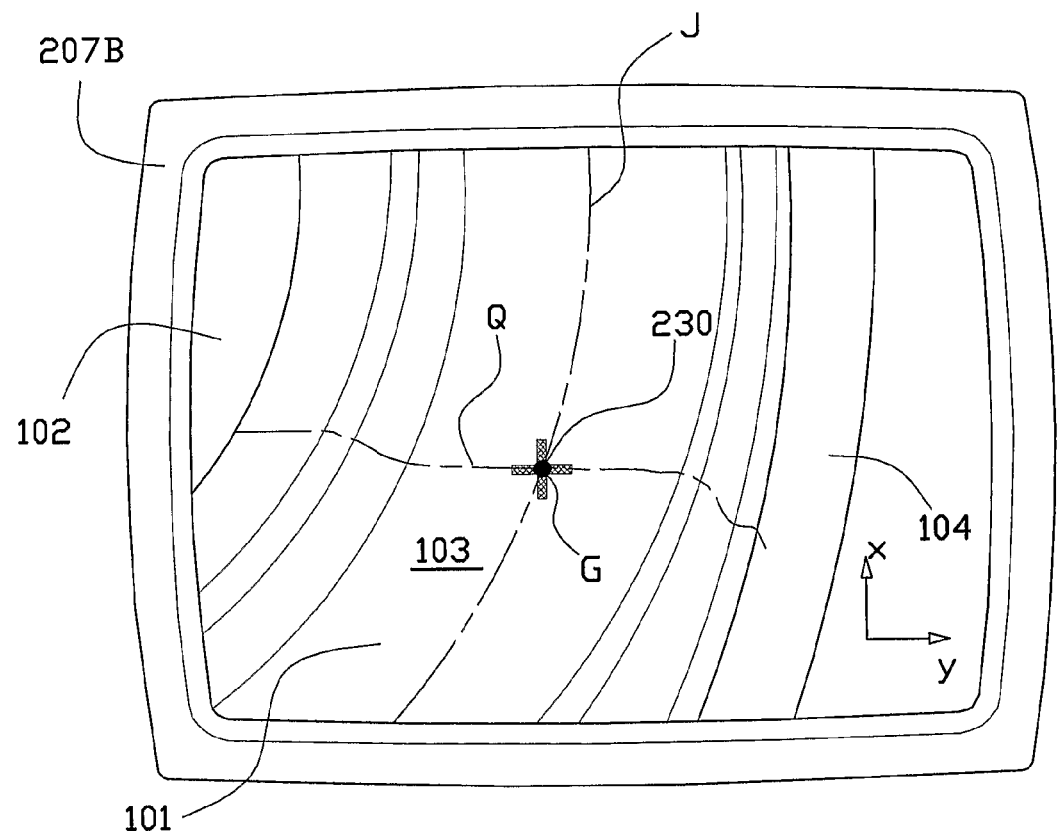

The radial runout measurement of the tyre 104 by the posterior pick-up device 209 includes locating at least a measuring plane K which is perpendicular to the wheel axis 100, which intersects the tread 108 surface, and positioning the posterior pick-up device 209, so that the laser beam R1 is directed towards a point of the tread 108 belonging to the measuring plane K (see FIG. 29).

At this point the wheel 100 is set in rotation and, during the rotation, the posterior pick-up device 209 is commanded to repeatedly measure its own distance from the tread 108, such as to detect the shape of the circumferential profile of the tread 108 in the measuring plane K.

In the invention the operation of locating the measuring plane K can be done in various ways.

A first way comprises preliminarily establishing the relative position of the measuring plane K with respect to the lateral flanks 110, 111 of the tyre 104.

For example, it can be established that the measuring plane K is in the centre of the wheel 100, exactly equidistanced from the lateral flanks 110, 111, or the measuring plane K can be set at a predetermined distance from one of the two external and internal lateral flanks 110 and 111.

This choice can be made by the operative via means for commanding the balancing machine 201, or can be automatically performed by the electronic calculator 204, on the basis of operating logic installed during programming thereof.

After having established the relative position of the measuring plane K, the posterior pick-up device 208 locates the effective position of the lateral flanks 110, 111 according to the procedure described herein above, i.e. by determining the distances Z3, Z4 of the lateral flanks 110, 111 from the reference planes F of the balancing machine 201.

Finally, on the basis of the effective position of the lateral flanks 110, 111 and the relative position of the measuring plane K, the electronic calculator 204 calculates the effective distance of the measuring plane K with respect to the reference plane of the balancing machine 201.

A second way of locating the measuring plane K comprises the operative's arbitrarily selecting from the images taken by the posterior camera 205, and displayed on the monitor 207A, the position of the measuring plane K at which he wishes to perform the radial runout measurement.

This choice is made totally autonomously, on the basis of the shape and size of the tread 108, the operative's experience and preferences.

Figure 27:
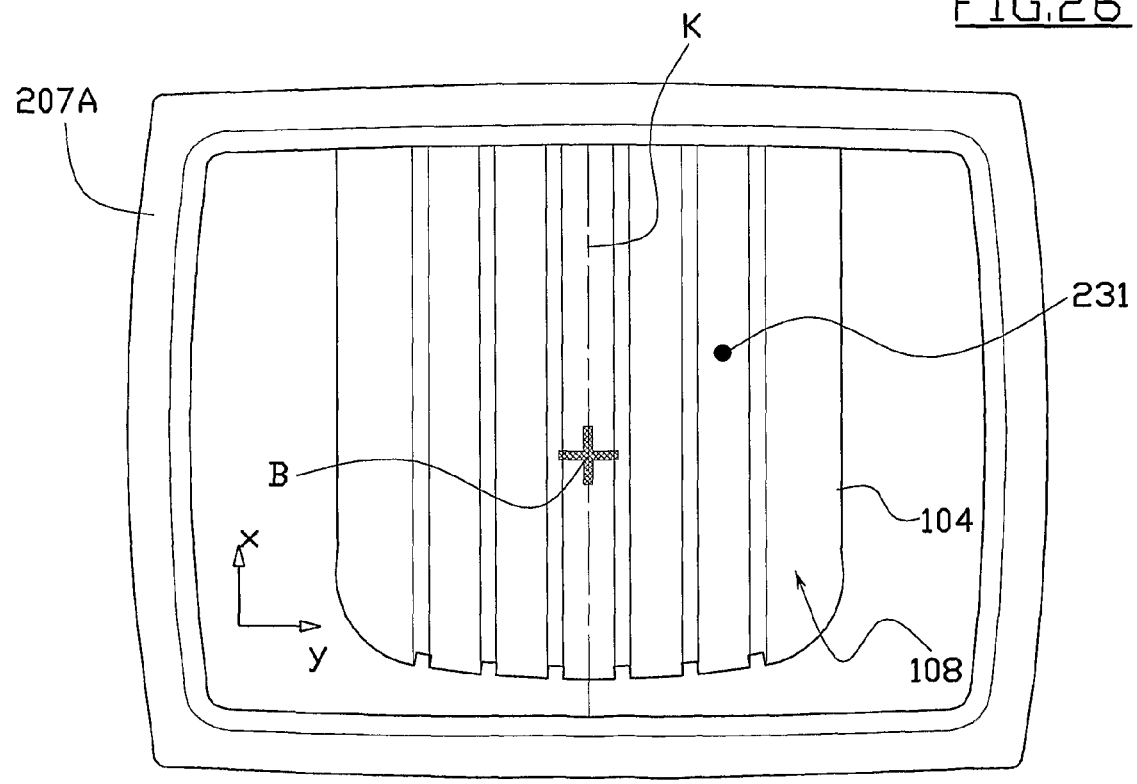

In particular (see FIG. 27), this selection is made by the operative's selecting a point B in the images, at a physical point on the tread 108 through which the pre-selected measuring plane K passes.

In this case, the images taken by the posterior camera 208 are directly managed by the calculator 204, which is programmed to enable the operative to select, on the monitor 207A, point B in the images, for example by direct contact, should the monitor 207A be a touch-screen, or using a mouse pointer, an optic pencil, a keyboard, a joystick or other known systems.

Once the selection has been made, the electronic calculator 204 recognises the selected point B, and acquires the coordinates thereof in a two-dimensional reference system xy which is fixed with respect to the image displayed on the monitor 207A.

Then, using these coordinates, the projection equation of the pre-selected measuring plane K (in the present example a vertical line) is determined, and possibly is also projected (superimposed) onto the images of the tread 208, in order for the operative to see it.

At this point, the electronic calculator 204 automatically activates the extensible arm 212 in order to position the posterior pick-up device 208 such that the laser beam R1 strikes a point on the tread 208 which corresponds to the measuring plane K selected on the images.

This positioning stage is managed according to a tracking process of the light trace of the laser beam R1, of a type used in the first embodiment for directing the pick-up devices 8, 9 towards the points on the tread 101 corresponding to the balancing planes E1, E2.

Briefly, from the images taken by the posterior camera 205, the electronic calculator 204 identifies the projection 231 of the light trace generated by the laser beam R1 on the tread 108 surface, and acquires the coordinates of the projection 231 in the reference system xy of the images.

Figure 28:
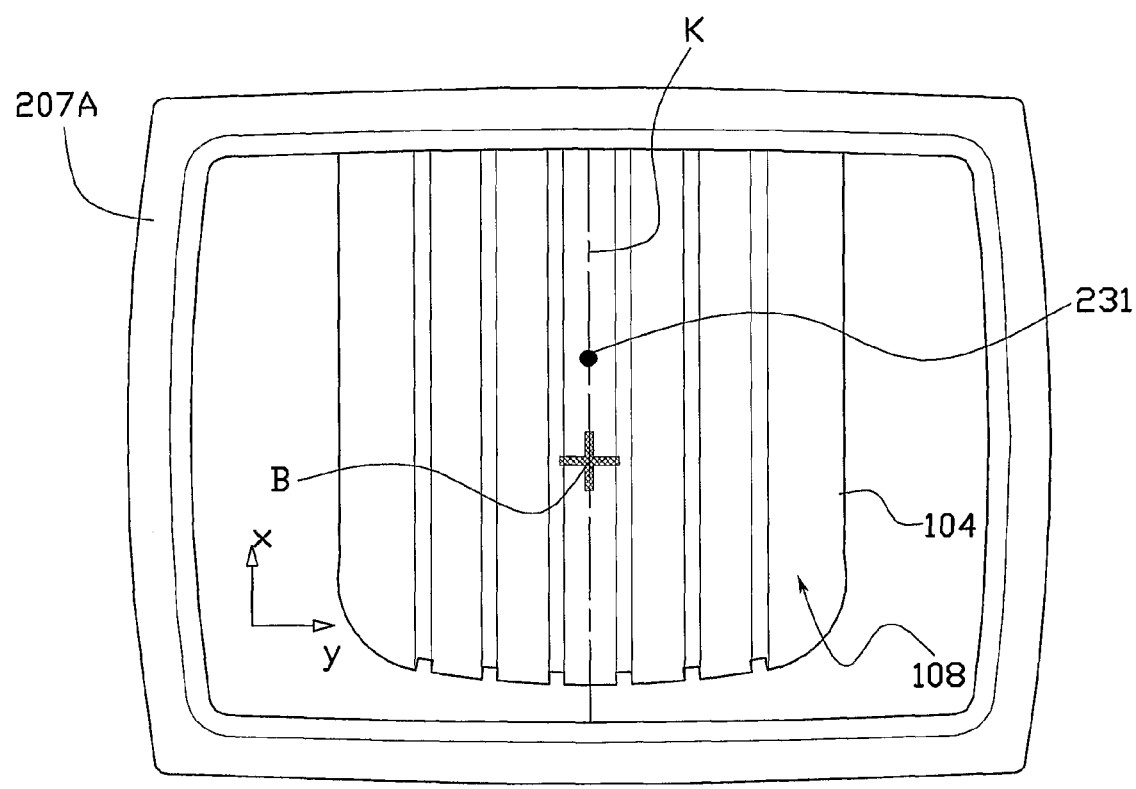

Then the electronic calculator 204 displaces the posterior pick-up device 208 up to when the projection 231 of the light trace superimposes on the pre-selected measuring plane K on the images (see FIG. 28).

Figure 34:
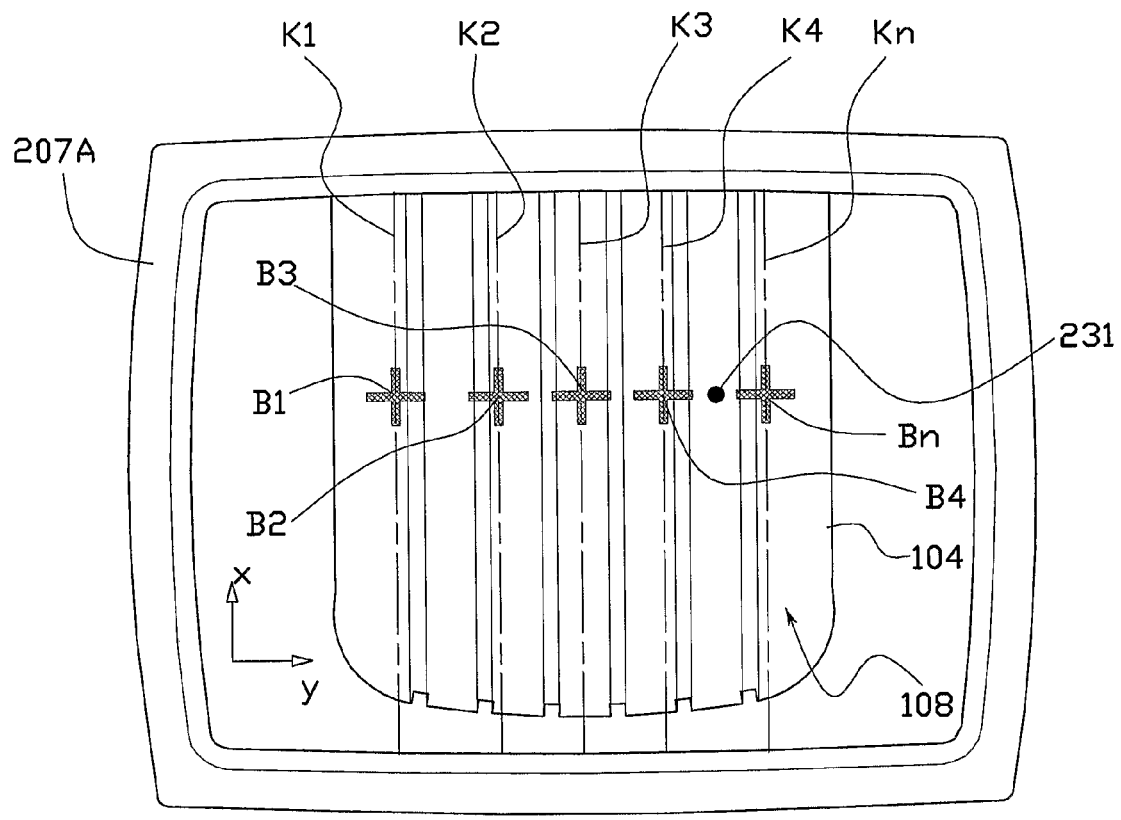
FIGS. 34 and 35 respectively show the images displayed by the monitor 207A and 207B in an alternative functioning mode of the machine of FIG. 1.

In a preferred embodiment of the invention illustrated in FIG. 34, the tyre 104 radial runout measurement is performed by locating a plurality of distinct measuring planes K1-Kn, perpendicular to the axis of the wheel 100 and intercepting the tread 108.

The posterior pick-up device 208 is then displaced in order to locate it in temporal succession in a plurality of distinct positions, in each of which the laser beam R1 is directed towards a point on the tread 108 which belongs to the respective measuring plane K1-Kn.

In each position, the pick-up device 208 is commanded to repeatedly measure, during the rotation of the wheel 100, its own distance from the tread 108, in order to detect the shape of the circumferential profile of the tread 108 in the relative measuring plane K1-Kn.

In this case too the location of the measuring planes K1-Kn can be performed according to any of the modalities described herein above.

Briefly, the following can be preliminarily established: the spatial position of the measuring planes K1-Kn with respect to the lateral flanks 110, 111 of the tyre 104, the location of the real position of the lateral flanks 110, 111, and finally the calculation of the real position of the measuring planes K1-Kn on the basis of the preceding information (in this case the balancing machine 201 does not have to be provided with the posterior camera 205).

The relative position of the measuring planes K1-Kn can be automatically established by the electronic calculator 204, or by a command given by the operative.

Alternatively, the measuring planes K1-Kn can be directly selected by the operative via the images taken by the posterior camera 205 and displayed on the monitor 207B, by selecting a plurality of points B1-Bn in the images which correspond to the physical points on the tread 108 from which the pre-selected measuring planes K1-Kn pass.

In addition, the invention includes a third mode of selection of the measuring planes K1-Kn, which is substantially a combination of the preceding modes. In the third mode, the operator chooses, on the images displayed on the monitor 207B, only two measuring planes K1 and Kn, with respect to which the electronic calculator 204 establishes the relative position of a plurality of further measuring planes K2-Kn−1.

In this way, the posterior pick-up device 205 is piloted with a tracking procedure on the light trace of the laser beam, such as to detect the real position only of the two pre-selected planes K1 and Kn, enabling the electronic calculator 204 to calculate the real position of the further measuring planes K2-Kn−1 on the basis of the information obtained.

Figure 33:
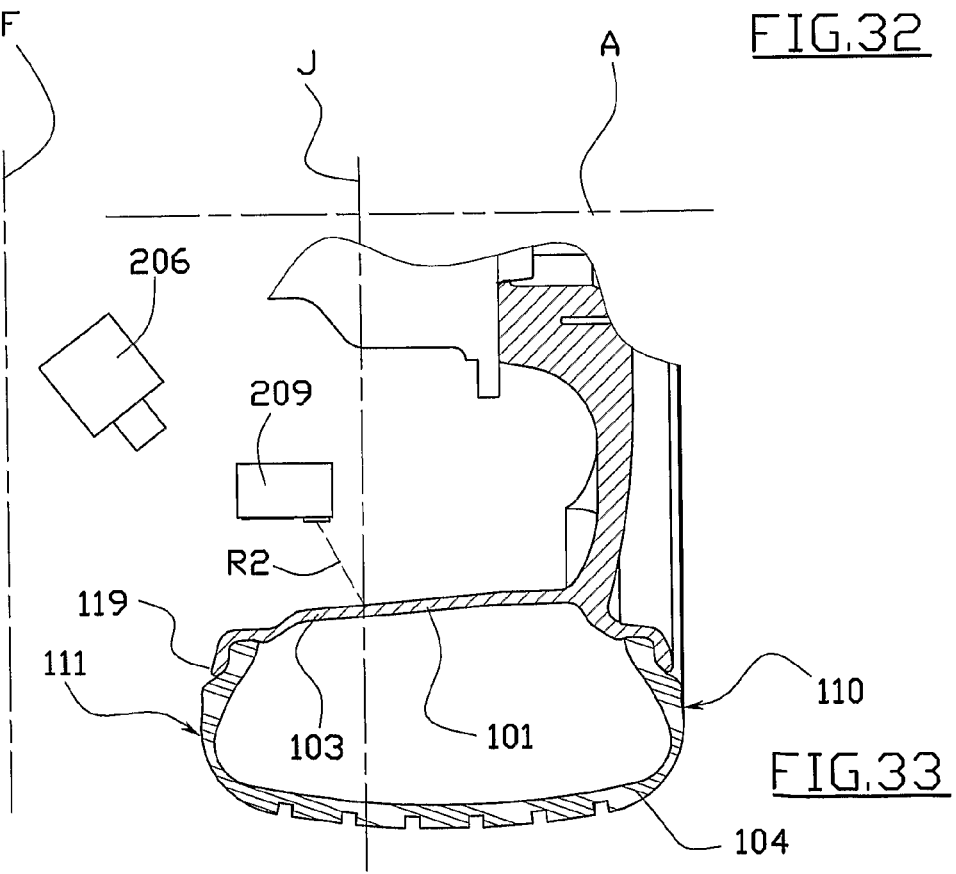
FIG. 33 shows the real position of the lateral pick-up device 209 at the instant shown in FIG. 32.

The radial runout measurement of the hub 101 by the lateral pick-up device 209 is done in an entirely similar way to what is described for the tread 108. In particular, it includes locating at least a measuring plane J which is perpendicular to the axis of the wheel 100, which intersects the surface of the channel of the hub 101, and positioning the lateral pick-up device 209, such that the laser beam R2 is directed towards a point on the hub 101 channel belonging to the measuring plane J (see FIG. 33).

At this point, the wheel 100 is set in rotation and during the rotation the lateral pick-up device 209 is commanded to repeatedly measure its own distance from the point on the channel of the hub 101 such as to detect the shape of the circumferential profile of the hub 101 in the measuring plane J.

The locating of the measuring plane J can be done following the same procedures as described herein above for measuring plane K.

The first procedure comprises preliminarily establishing the relative position of the measuring plane J with respect to the lateral flanks 110, 111 of the tyre 104 of the wheel 100 to be measured; locating the real position of the lateral flanks 110, 111 of the wheel 100; and calculating the effective position of the measuring plane J, on the basis of the effective position of the lateral flanks 110, 111 and the relative position of the measuring plane J with respect thereto.

The second procedure comprises the operative's autonomously choosing, from the images taken by the lateral camera 206 and displayed on the monitor 208B, the position of the measuring plane J at which he wishes to perform the radial runout measurement. This choice is made by the operator by selecting a point G in the images at a physical point in the channel of the hub 101 from which the pre-selected measuring plane J passes.

Possibly, in order to facilitate the choice, the laser projector 211 can be activated, which projector 211, by generating the visible light line Q on the surface of the hub 101 channel, provides a visual aid to the selection of point G.

Once the selection has been made, the electronic calculator 204 recognises the selected point G and can general a visible signal on the monitor 208B, which might be, for example, a cross evidencing the choice made.

In the example illustrated in the figures, the pre-selected point G is a point of the visible light line Q; however, this is not a necessary condition, as point G can also be a point that is external of the visible light line Q.

At this point the electronic calculator 204 automatically activates the extensible arm 213, in order to position the lateral pick-up device 209 so that the laser beam R2 can strike a point in the channel of the hub 101 located at the selected point G in the images.

This positioning stage can be done following any tracking procedure of the light trace of the laser beam R2, of the type used in the first embodiment for directing the pick-up devices 8, 9 towards the points on the hub 101 at the balancing planes E1, E2.

Figure 35:
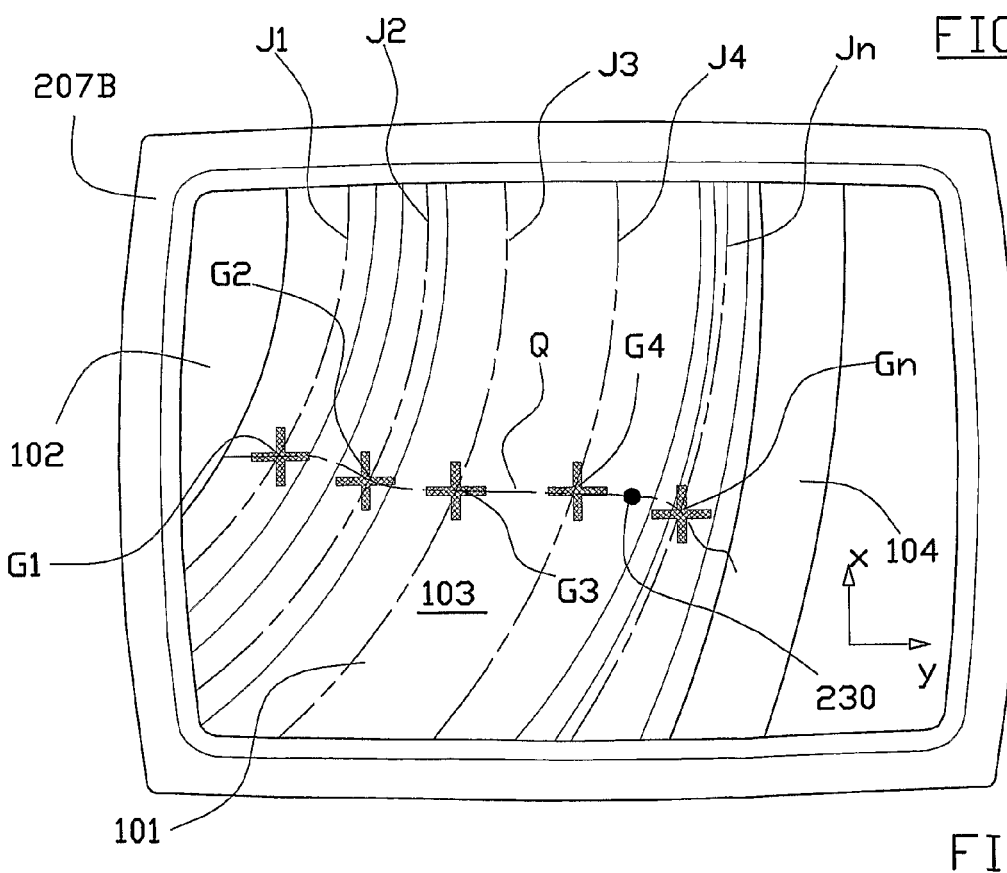

In this case too, the radial runout of the hub 101 is preferably performed on a plurality of distinct measuring planes J1-Jn, perpendicular to the wheel 100 axis and intercepting the channel of the hub 101, each of which can be located in one of the procedures illustrated for the locating of the measuring planes K1-Kn; for example, by selecting a plurality of points G1-Gn in the images, each of which is at a physical point of the channel 103 of the hub 101 from which a respective pre-selected measuring pale H1-Jn passes (FIG. 35).

In this case too, differently to what is illustrated in the images, the points G1-Gn might not belong to the visible light line Q.

With the aid of figures from 36 to 42, an alternative operating mode of the balancing machine 201 is described which enables greater information to be obtained relating to the geometry of the rim 109 of the hub 101, in order for the automatic locating of the balancing planes to be presented to the user to be more precise, rapid and reliable.

In order to provide a context for this mode of operation, first some observations will be made relating to the rim edge 109 of the hub 101 which connects the hub 101 to the tyre 104.

Figure 37:
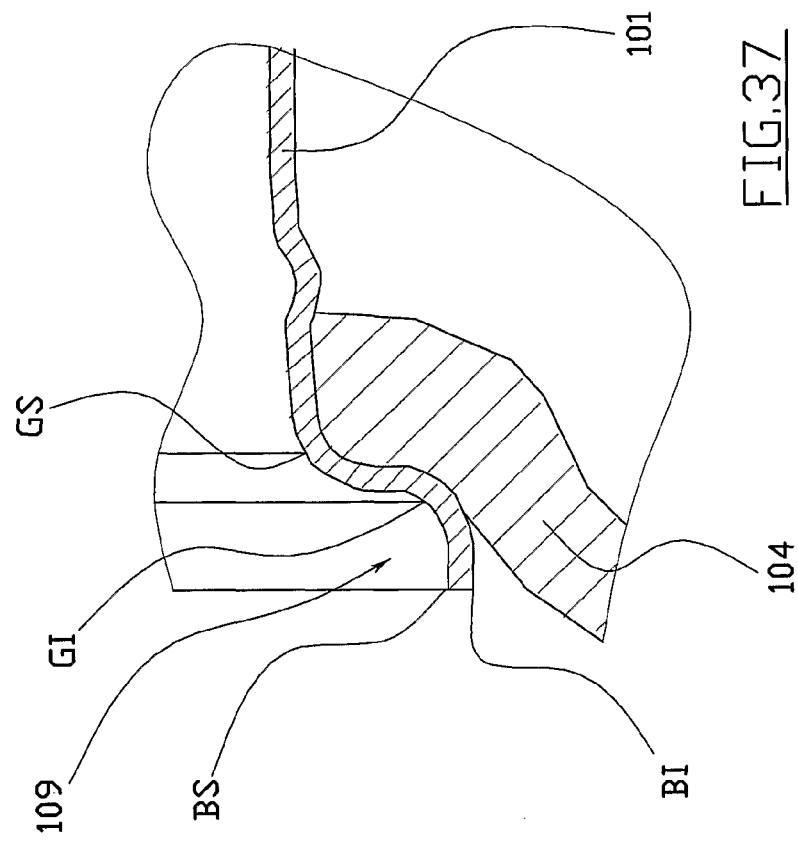
FIGS. 36 and 37 are two details showing, in section, further possible shapes of the rim edges 109 of a hub 101.
Figure 36:
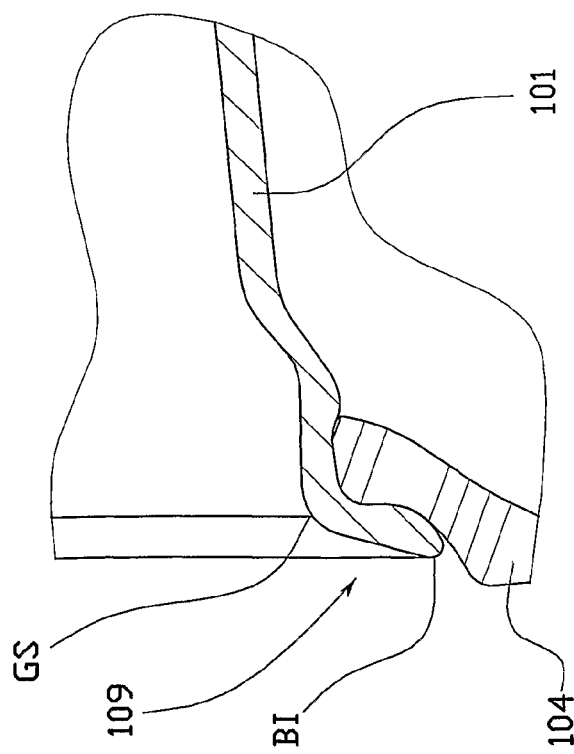

The rim edge 109, in the majority of hubs 101 at present on the market, can exhibit a substantially L-shaped section, as illustrated in FIG. 36, or can have a substantially S-shaped section, as illustrated in FIG. 37.

In both cases, this shape means that at the rim 109 numerous circumferences are concentrated which are characteristic of the hub 101, which are at different distances from the reference plane F of the balancing machine 201 and which can have significantly different diameters from one another.

For example, at the L-shaped rim 109 of FIG. 36, there are generally two characteristic circumferences, passing respectively through point BI, called the lower rim, and point GS, known as the upper bend; while at the S-shaped rim 109 in FIG. 37. there are generally four characteristic circumferences, which pass respectively through point BI, the lower rim, point BS, the upper rim, and point GS, the upper bend.

As shown in FIG. 38 for the S-shaped rim 109 (but the same observations are valid for the L-shaped rim too), the curves C4-C7 representing the circumferences at the rim of the hub 101 in the images taken by the lateral camera 206 are much closer to one another.

For this reason, the process of locating the rim edge 109 of the hub 101 based on the processing of the images, as described for the previous embodiment, might theoretically lead to the final selection of any of the curves C4-C7 by chance. This degree of chance does not compromise the correct functioning of the balancing machine 201, but could however be overcome using the alternative mode which will be described herein below. The alternative mode comprises the electronic calculator 204 acquiring the photographs of the hub taken by the lateral camera 206, and performing a preliminary analysis to identify a plurality of curves C1-Cn representing the hub 101 on the photographs, as occurs in the preceding embodiment (see FIG. 38).

At this point, a first delimiting plane I1 and a second delimiting plane I2 are chosen, perpendicular to the axis A of the wheel 100, between which an annular strip of the wheel 100 is comprised, which includes the rim of the hub 101 (see FIG. 42).

In particular, the choice of the delimiting planes 11 and 12 is established by defining the distance of each of the planes with respect to the reference plane F of the balancing machine 201.

Since the annular strip must comprise the rim of the hub 101, the first delimiting plane I1 is distanced from the reference plane F by a substantially equal amount to the distance Z4 of the internal flank 111 of the tyre 104, and the second delimiting plane I2 is positioned towards the inside of the wheel, at a predetermined distance Z6 from the first delimiting plane I1.

The distance Z4 between the internal flank 11 of the tyre 104 and the reference plane F is measured by the posterior pick-up device 208 according to one of the modes described for the preceding embodiment.

Once the position of the delimiting planes 11 and 12 has been established, the lateral pick-up device 209 is located in an initial operating position, in which the laser beams R2 is directed at a point of the internal flank 11 of the tyre 104 of the wheel 100 which belongs to the first delimiting plane I1 (see FIG. 42).

As the laser beam R2 is inclined with respect to the advancement direction of the lateral pick-up 209, and the diameter of the wheel 100 is variable in an axial direction, in order to direct the laser beam R2 to the point on the tyre 104, apart from knowing the distance Z4 it is necessary to perform a similar procedure to the one described for the preceding embodiment in order to direct the laser beam R2 onto the point P1 of the balancing plane E1.

For example, starting from a first position at the side F of the support structure, the lateral pick-up device 209 can be advanced in an axial direction by quantity Z4. After this advance, the laser beam R2 will generally strike a point of the hub 101 which does not belong to the delimiting plane I1, but whose distance from the reference plane F can be calculated by means of the lateral pick-up device 209. In this way, the electronic calculator 204 calculates the distance of the point on the hub 101 with respect to the delimiting plane I1, and commands the lateral pick-up device 209 to reverse by a quantity which is equal to the calculated distance. Then the procedure is repeated up until the calculated distance falls below a predetermined threshold value.

When the procedure has been completed, the lateral pick-up device 209 is in the desired operating position, in which the laser beam R2 is directed towards a point on the internal lateral flank 11 of the tyre 104 of the wheel 100 belonging to the first delimiting plane.

Figure 39:
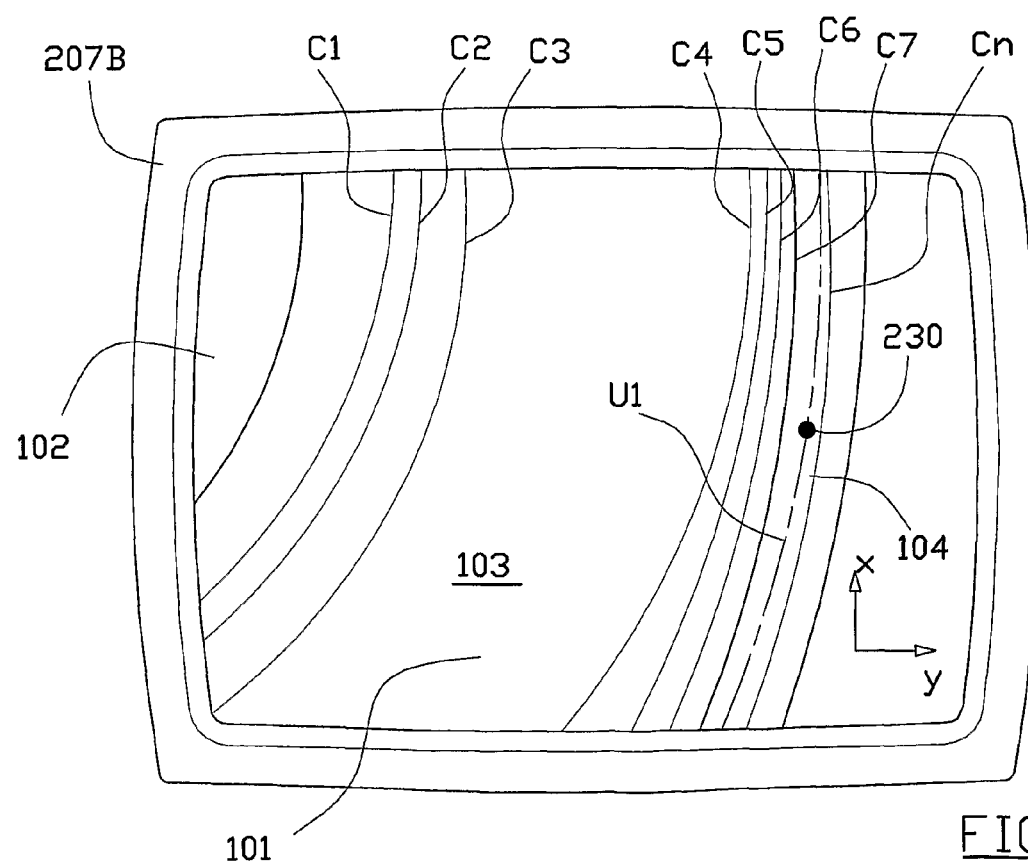

With the lateral pick-up device 209 in this initial operating position, the electronic calculator 204 can generate, on the images taken by the lateral camera 206, a first demarcation curve U1, which has a similar shape to the previously-identified characteristic curves C1-Cn and passes through the projection 230 of the laser trace, such as to signal the confines of the pre-selected annular strip on the monitor 207B (see FIG. 39).

Starting from the initial operating position, the lateral pick-up device 209 is advanced in an axial direction, such as to displace the laser beam R2 towards the second delimiting plane I2.

The advancement is controlled automatically by the electronic calculator 204, by means of a tracking procedure of the projection 230 of the light trace of the laser beam R2 on the images taken by the lateral camera 206, of the type of those used and described in the preceding embodiment.

Figure 40:
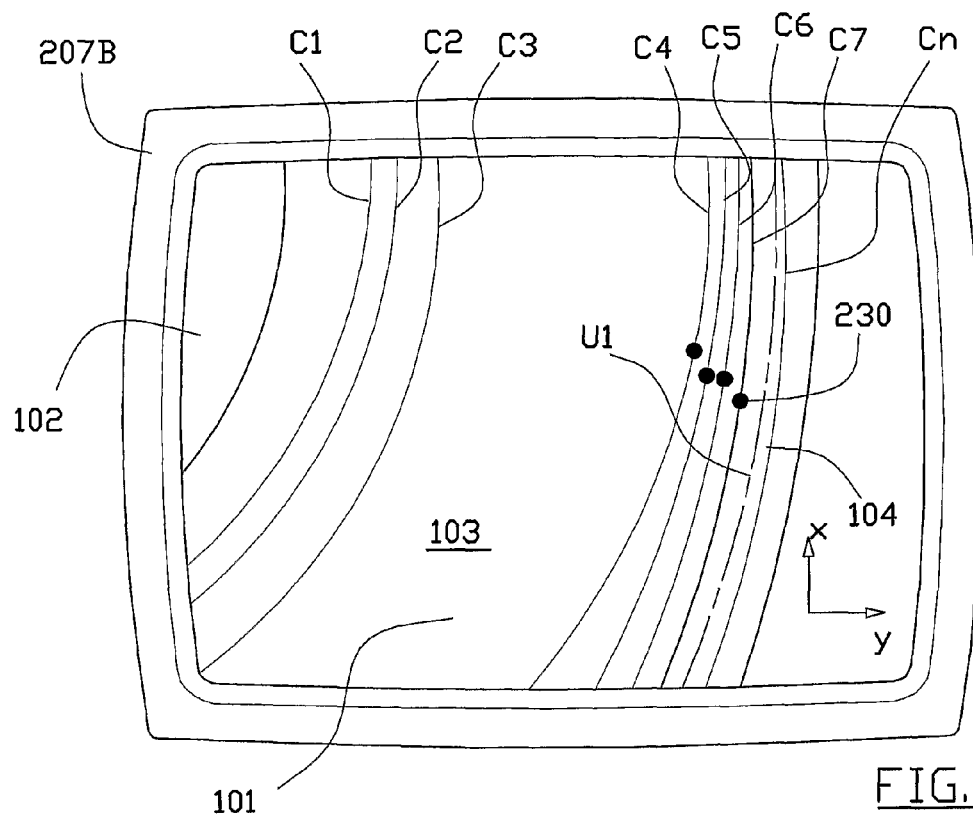

In particular, during the advancement run, the electronic calculator 204 stops the lateral pick-up device 209 each time the projection 230 of the light trace intersects one of the curves C1-Cn previously identified in the images (see FIG. 40).

In this way, for each stop of the lateral pick-up device 209, the laser beam R2 will be directed towards a point of the hub which belongs to a characteristic circumference of the rim of the hub 101. For each stop, the lateral pick-up device 209 is commanded to measure the distance of the point struck, such that the electronic calculator 204 can calculate the diameter of the characteristic circumference passing through the point, as well as the distance of the characteristic circumference from the reference plane F of the balancing machine 201.

The advancing of the lateral pick-up device 209 proceeds to perform a full run, starting from the initial operating position, which is the set distance Z6 between the first and the second delimiting plane I1 and I2. After having run the above-mentioned distance Z6, the lateral pick-up devices 209 will generally be in an intermediate position, in which the laser beam R2 is not directed towards a point on the hub which belongs to the second delimiting plane I2; this is due to the inclination of the laser beam R2 and the variability of the wheel 100 diameter in the axial direction.

Starting from this intermediate operating position, the lateral pick-up device 209 can be displaced according to a procedure by steps which are the same as the ones previously described, up until it is located in a final operating position in which the laser beam R2 is directed at a point on the hub 101 belonging to the second delimiting plane I2.

Obviously, if during the further displacement the projection 230 of the laser trace intersects a further characteristic curve of the set C1-Cn, the lateral pick-up device 209 is immediately arrested, in order to measure the diameter of the hub 101 circumference passing through that point, and the distance of the circumference itself from the reference plane F of the balancing machine 201.

Figure 41:
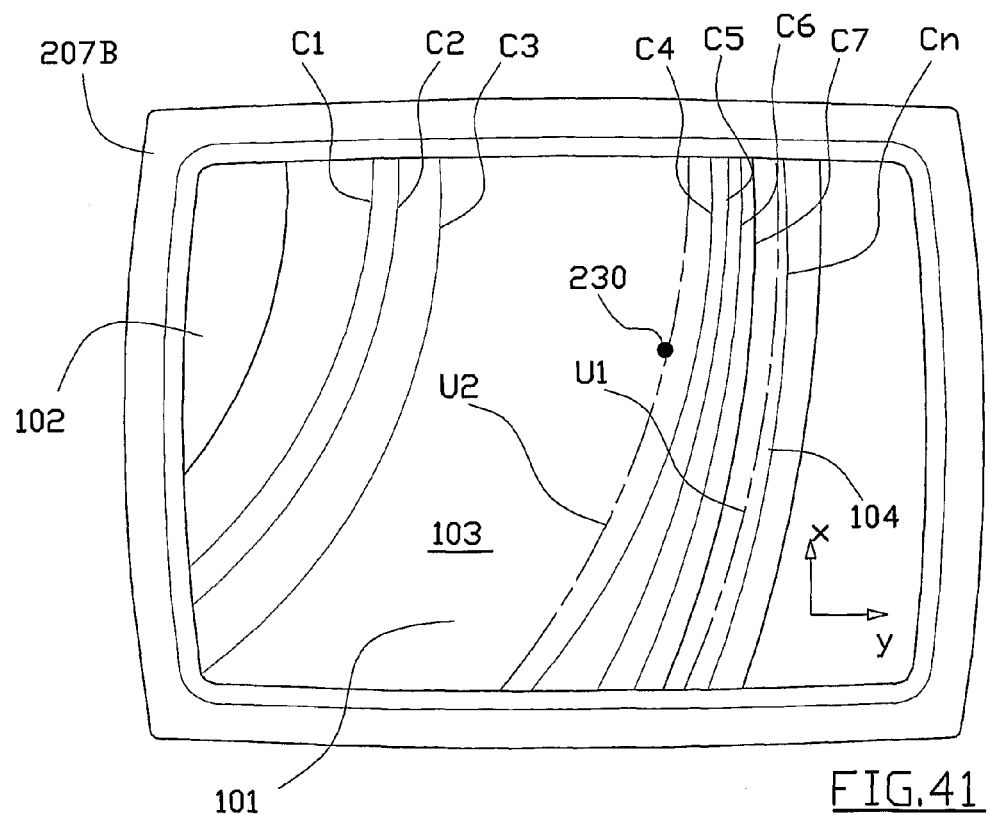

When the lateral pick-up device 209 reaches the final operating position, the electronic calculator 204 can generate, on the images taken by the lateral camera 206, a second demarcation curve U2 having a similar shape to the characteristic curves C1-Cn previously identified and passing through the projection 230 of the laser trace, in order to signal the confines of the considered annular strips on the monitor 207B (see FIG. 41).

At the end of the described procedure, the electronic calculator 204 has thus acquired the characteristic parameters of the hub 101 for all of the circumferences contained in the considered annular strip, i.e. for those represented by the characteristic curves of the set C4-C7 which in the images are internal of the two demarcation curves U1 and U2; while the electronic calculator 204 has completely ignored all the circumferences represented by the characteristic curves found on the outside of the demarcation curves U1 and U2.

In particular, the circumferences of which the electronic calculator 204 has acquired the characteristic parameters are those which are at the rim of the hub 101, i.e. they are those passing respectively through the lower rim points B1, upper rim points BS, the lower bend GI and the upper bend curve GS.

In this way, on the basis of the characteristic parameters of each of the circumferences, the electronic calculator 204 can select the best circumference for proceeding with the identification of the optimal balancing planes to be proposed to the user.

For example, in the illustrated case, in which the rim of the hub 101 is S-shaped, the electronic calculator 204 will preferably select the circumference passing through the point of the lower bend GI, while in the case in which the rim of the hub 101 is L-shaped, the electronic calculator 204 will preferably select the circumference passing through the upper bend GS.

To conclude, note that the functioning modes and the technical solutions described by the single balancing machines 1 and 201 can be combined such as to obtain a single balancing machine which possesses some or all of the functions and the technical solutions of the balancing machines described 1 and 201.

Obviously an expert in the sector might make numerous modifications of a technical-applicational nature to the balancing machines 1 and 201, without its forsaking the ambit of the invention as is claimed herein below.

The invention claimed is:

1. A method for balancing a vehicle wheel using at least one weight (18), comprising the steps of:
    using a video camera (5, 6, 206) to frame a portion of a surface of a hub (101) of the wheel on which the at least one weight (18) is to be applied;
    locating, in images of the hub (101) taken by the camera (5, 6, 206), at least one balancing plane (E1, E2) which is perpendicular to a rotation axis (A) of the wheel, piloting at least one pick-up device (8, 9, 209) such as to direct the at least one pick-up device (8, 9, 209) onto a point (P1, P2) of the hub (101) which belongs to the at least one balancing plane (E1, E2), detecting, by means of the at least one pick-up device (8, 9, 209) characteristic geometric parameters of the hub (101) at the at least one balancing plane (E1, E2),
    measuring an imbalance of the wheel,
    calculating, by means of an electronic calculator (4, 204), an entity of at least one weight (18) to be applied to the hub (101) at the at least one balancing plane (E1, E2), and an angular position (T1, T2) of the at least one weight (18) in the at least one balancing plane (E1, E2),
    characterized in that the step of locating the at least one balancing plane (E1, E2) includes:
    identifying, in the images of the hub (101) taken by the camera (206), at least one reference line (C) corresponding to a circumference of the surface of the hub (101).

2. The method of claim 1, characterised in that identification of the at least one reference line (C) comprises the electronic calculator (204) acquiring at least one image of the hub (101) taken by the camera (206), and subjecting at least one image to an analytical processing for recognising the predetermined at least one reference line (C) in at least one image.

3. The method of claim 2, characterized in that the analytical processing of the at least one image is aimed at recognising the transition zone between the hub (101) and a tyre (104) in the at least one image.

4. The method of claim 2, characterized in that the at least one image is acquired in a condition in which a portion of the hub (101) taken by the camera (209) is illustrated by at least one light.

5. The method of claim 1, characterized in that the predetermined reference line (C) corresponds to a rim (109) edge of the hub (101).

6. The method of claim 1, characterized in that the stage of locating the at least one balancing plane (E1, E2) further comprises:
  establishing a distance (L1, L3) between the at least one balancing plane (E1, E2) and the circumference of the hub (101) which is represented by the reference line (C) identified on the at least one image.

7. The method of claim 6, characterized in that the stage of piloting the at least one pick-up device (209) includes further displacing the at least one pick-up device (209) in a parallel direction to the axis A of the wheel (100), by a quantity equal to a distance (L1, L3) established between the at least one balancing plane (E1, E2) and the circumference of the hub (101) which is represented by the at least one reference line (C) identified by the at least one image.

8. The method of claim 1, characterized in that the stage of piloting the at least one pickup device (209) includes displacing the at least one pick-up device (209) up until it is directed onto a point of the hub (101) which belongs to the circumference represented by the at least one reference line (C) identified on the at least one image.

9. The method of claim 8, characterized in that the at least one pick-up device (209) generates a light trace on the surfaces of the hub (101) onto which it is directed, and that the displacement of the at least one pick-up device (209) proceeds up until a projection (230) of the light trace on the at least one image is at the at least one reference line (C).

10. The method of claim 9, characterized in that the displacement of the at least one pick-up device (209) is controlled by the electronic calculator (204), which processes the images taken by the camera (206) in order to detect, in a predetermined two-dimensional reference system (xy) of the at least one image, the position of the projection of the light trace generated by the at least one pick-up device (209) and the identified at least one reference line (C).

11. The method of claim 1, characterized in that the stage of locating the at least one balancing plane (E1, E2) includes:
  identifying, in the at least one image of the wheel taken by the camera (206), a plurality of reference lines (C4-C7), each of which represents a circumference belonging to a predetermined annular strip of the wheel (100);
  displacing the at least one pick-up device (209) in order to direct it onto a plurality of points on the wheel (100), each of which belongs to one of the circumferences in the annular strip of the wheel (100) and which points are singly represented by the reference lines (C4-C7) identified on the at least one image,
  measuring the characteristic parameters of the hub (101) in the said points by means of the at least one pick-up device (209).

12. A method for balancing a vehicle wheel using weights (18), comprising the steps of:
  using a video camera (5, 6, 206) to frame a portion of a surface of a hub (101) of a wheel on which a weight (18) is to be applied;
  locating, in images of the hub (101) taken by the camera (5, 6, 206), at least one balancing plane (E1, E2) which is perpendicular to a rotation axis (A) of the wheel,
  piloting at least one pick-up device (8, 9, 209) such as to direct the at least one pick-up device (8, 9, 209) onto a point (P1, P2) of the hub (101) which belongs to the at least one balancing plane (E1, E2),
  detecting, by means of the at least one pick-up device (8, 9, 209) characteristic geometric parameters of the hub (101) at the at least one balancing plane (E1, E2),
  measuring an imbalance of the wheel,
  calculating, by means of an electronic calculator (4, 204), an entity of at least one weight (18) to be applied to the hub (101) at the at least one balancing plane (E1, E2), and an angular position (T1, T2) of the at least one weight (18) in the at least one balancing plane (E1, E2),
  characterised in that the stage of locating the at least one balancing plane (E1, E2) includes:
  projecting the images taken by the at least one camera (5, 6) on a screen (7), and
  arbitrarily selecting the at least one balancing plane (E1, E2) from the images projected on the screen (7).

13. The method of claim 12, characterized in that the piloting of the at least one pick-up device (8, 9) includes the at least one pick-up device (8, 9) generating a light trace (200) on the surfaces of the hub (101) onto which the at least one pick-up device (8, 9) is directed, and in that the at least one pick-up device (8, 9) is displaced up until the projection (20) of the light trace (200) on the images is located at the pre-selected at least one balancing plane (E1, E2).

14. The method of claim 13, characterized in that the displacement of the at least one pick-up device (8, 9) is controlled by a manual selector (14) activated directly by an operative, which operative, via the screen (7), observes movement of the projection (20) of the light trace (200) in the images.

15. The method of claim 13, characterized in that the displacement of the at least one pick-up device (8, 9) is controlled by the electronic calculator (4), which processes the images taken by the camera (5, 6) in order to detect, in a predetermined two-dimensional reference system (xy) which is fixed with respect to the images, a position of the projection (20) of the light trace (200) and the projection (E1', E2') of the pre-selected at least one balancing plane (E1, E2).

16. The method of claim 13, characterized in that the images taken by the camera (5, 6) are processed by the electronic calculator (4), which is programmed to perform the steps of:
  memorising a base image of the wheel surfaces taken by the camera (5, 6),
  moving the at least one pick-up device (8, 9) such that the light trace (200) displaces on the surfaces of the images taken by the camera (5, 6) along a predetermined trajectory,
  detecting, in a predetermined two-dimensional system (xy) of the images, coordinates of the projection (20) of the light trace (200) in a plurality of distinct positions along the trajectory,
  memorising the spatial position of the at least one pick-up device (8, 9) at each position in which detection of the position of the projection (20) of the light trace (200) is made, projecting the base image onto the screen (7) and signalling thereon the points at which the instantaneous coordinates have previously been detected.

17. The method of claim 16, characterized in that the step of choosing the at least one balancing plane (E1, E2) is done by selecting, from among the points signalled on the base image, a point which is located at the pre-selected balancing plane (E1, E2).

18. The method of claim 17, characterized in that the step of positioning the at least one pick-up device (8, 9) includes:
   arranging the at least one pick-up device (8,9) in the memorised spatial position in which the projection (20) of the light trace (200) is at the selected point on the base image.

19. The method of claim 12, characterized in that the images taken by the camera (5, 6) are processed by the electronic calculator (4), which calculator (4) is programmed to enable selection of the points (P1', P2') in the images, and in that selection of the at least one balancing plane (E1, E2) is done by selecting a point (P1', P2') in the images at the first pre-selected balancing plane (E1, E2).

20. A machine for balancing a vehicle wheel using weights (18), comprising a rotating shaft (3, 203) which rotates on a fixed structure (2, 202), means for blocking the wheel on the rotating shaft (3, 203), means for measuring an imbalance of the wheel, an electronic calculator (4, 204) for calculating entities of the weights (18) to be applied to a hub (101) of the wheel (100) in at least one preselected balancing plane (E1, E2) which is perpendicular to the axis (A) of the wheel and the angular position of the weights (18) in the at least one balancing plane (E1, E2), at least one camera (5, 6, 206) for framing a portion of the hub (101) in which weights (18) are to be applied, a screen (7, 207B) on which images taken by the camera (5, 6 206) are projected, and at least one pick-up device (8, 9, 209), connected to the electronic calculator (4, 204), which is destined to be piloted in order to be directed on to a point (P1, P2) on the hub (101) which belongs to the at least one balancing plane (E1, E2), characterised in that it comprises means for acquiring a plurality of distinct images of the hub (101), in a predetermined temporal order and under different conditions in order to identify at least one reference line (C) corresponding to a circumference of the surface of the hub (101).

21. The machine of claim 20, characterized in that the pick-up device (8, 9, 209) is an optical device for measuring distances which comprises means for detecting a position of a point on the hub (101) in relation to a preselected known reference system (XYZ).

22. The machine of claim 20, characterized in that the pick-up device (8, 9, 209) is associated to means for activating (12, 13, 213) for moving the pick-up device (8, 9, 209) with respect to the balancing machine.

23. The machine of claim 22, characterized in that the pick-up device (8, 9, 209) generates a light trace (200) on the surface of the hub (101), at the measuring point.

24. The machine of claim 23, characterized in that the camera (5, 6, 206) is connected to the electronic calculator (4, 204), which comprises a program for processing and projecting the images on the screen (7, 207B), and is connected to the means for activating (12, 13, 213) of the pick-up device (8, 9, 209).

25. The machine of claim 23, characterized in that the electronic calculator (4, 204) comprises a program for detecting a position on the images of the projection (20, 230) of the light trace (200) of the pick-up device (8, 9, 209), with respect to a two-dimensional reference system (xy) which is fixed with respect to the images, and for commanding the means for activating the pick-up device (8, 9, 209) in order to position the projection (20, 230) of the light trace (200) in a position on the images.

26. The machine of claim 25, characterized in that it comprises means, connected to the electronic calculator (4), for selecting a point (P1', P2') in the images projected on the screen (7), and in that the electronic calculator (4) comprises a program for detecting a position of the point (P1', P2') with respect to the two-dimensional reference system (xy) of the images.

27. The machine of claim 26, characterized in that the means for selecting a point (P1', P2') comprise a touchscreen monitor, which also functions as the monitor screen (7).

28. The machine of claim 22, characterized in that the means for activating (12, 13) are commanded by a manual selector (14) which is directly activated by an operative.

29. The machine of claim 20, characterized in that it comprises at least a lighting device (210) arranged in order to illuminate a portion of the hub (101) surface framed by the camera (206).

* * * * *